(12) United States Patent
Alanine et al.

(10) Patent No.: US 7,781,441 B2
(45) Date of Patent: Aug. 24, 2010

(54) (3,4-DIHYDRO-QUINAZOLIN-2-YL)- (2-ARYLOXY-ETHYL)-AMINE

(75) Inventors: Alexander Alanine, Schlierbach (FR); Luca Claudio Gobbi, Oberwil (CH); Sabine Kolczewski, Rheinfelden (DE); Thomas Luebbers, Loerrach (DE); Jens-Uwe Peters, Grenzach-Wyhlen (DE); Lucinda Steward, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 1072 days.

(21) Appl. No.: 11/412,432

(22) Filed: Apr. 27, 2006

(65) Prior Publication Data

US 2006/0252779 A1     Nov. 9, 2006

(30) Foreign Application Priority Data

May 4, 2005    (EP) .................................. 05103744

(51) Int. Cl.
*A61K 31/517* (2006.01)
*C07D 239/84* (2006.01)
*C07D 239/70* (2006.01)
(52) U.S. Cl. .................... 514/266.4; 514/267; 544/249; 544/292
(58) Field of Classification Search .............. 514/266.4, 514/267; 544/249, 292
See application file for complete search history.

(56) References Cited

U.S. PATENT DOCUMENTS 3,496,179 A * 2/1970 Hess .............. 544/292
2006/0025406 A1* 2/2006 Zembower et al. .......... 514/218

FOREIGN PATENT DOCUMENTS

WO  WO 02/18348       3/2002
WO  WO 2004/087680   10/2004
WO  WO 2004/096771   11/2004

OTHER PUBLICATIONS

Hoyer, et al., Pharmacol. Rev. vol. 46, pp. 157-204 (1994).
Rees et al., FEBS Letters, vol. 355, pp. 242-246 (1994).
Francken et al., Eur. J. Pharmacol. vol. 361, pp. 299-309 (1998).
Noda, et al., J. Neurochem. vol. 84, pp. 222-232 (2003).
Dubertret et al., Journal of Psychiatric Research, vol. 38, pp. 371-376 (2004).
Manetsch, et al., Chem. Eur. J., vol. 10, pp. 2487-2506 (2004).
Aronov et al., J. Med. Chem, 2008, pp. 1214-1222.
Peters, et al., ChemMedChem 2009, vol. 4, pp. 680-686.

* cited by examiner

*Primary Examiner*—James O Wilson
*Assistant Examiner*—Tamthom N Truong
(74) *Attorney, Agent, or Firm*—George W. Johnston; Patricia S. Rocha-Tramaloni; Kimberly J. Prior

(57) ABSTRACT

The present invention relates to compounds of formula I

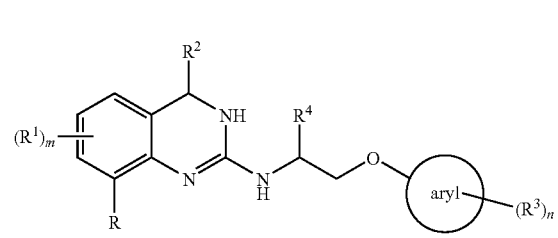

wherein
$R$, $R^1$, $R^2$, $R^3$, $R^4$, aryl, n, and m are as defined in the specification and pharmaceutically acceptable acid addition salts and tautomeric forms thereof. Such compounds have good activity on the $5\text{-HT}_{5A}$ receptor. Therefore, the invention provides methods for the treatment of certain CNS disorders with such compounds.

24 Claims, No Drawings

(3,4-DIHYDRO-QUINAZOLIN-2-YL)-(2-ARYLOXY-ETHYL)-AMINE

PRIORITY TO RELATED APPLICATIONS

This application claims the benefit of European Application No. 05103744.8, filed May 4, 2005, which is hereby incorporated by reference in its entirety.

BACKGROUND OF THE INVENTION

The neurotransmitter 5-hydroxytryptamine (5-HT, serotonin) modulates a wide range of physiological and pathological processes in the central nervous system and periphery, including anxiety, sleep regulation, aggression, feeding and depression (Hoyer et al., *Pharmacol. Rev.* 46, 157-204, 1994). Both pharmacological characterization and molecular cloning of several 5-HT receptor genes has revealed that 5-HT mediates its diverse physiological actions through a multiplicity of receptor subtypes. These receptors belong to at least two different protein superfamilies: ligand-gated ion channel receptor (5-HT$_3$) and the G-protein-coupled 7-transmembrane receptors (thirteen distinct receptors cloned to date). In addition, within the G-protein-coupled receptors, serotonin exerts its actions through a multiplicity of signal transduction mechanisms.

The cloning and characterization of the human 5-HT$_{5A}$ serotonin receptor has been described in *FEBS Letters*, 355, 242-246 (1994). The sequence is not closely related to that of any previously known serotonin receptor, with the best homology being 35% to the human 5-HT$_{1B}$ receptor. It encodes a predicted 357 amino-acid protein, with seven putative transmembrane domains, consistent with that of a G-protein coupled receptor. The sequence is characterized by containing an intron between transmembrane domains V and VI. More recently coupling to Gi/o α mechanisms has been demonstrated with the inhibition of forskolin stimulated cAMP and also evidence for more complicated G-protein mediated coupling mechanisms have been proposed (Francken et al. *Eur. J. Pharmacol.* 361, 299-309, 1998; Noda et al., *J. Neurochem.* 84, 222-232, 2003). Furthermore, in WO 2004/096771 it is described the use of compounds, which are active on the 5-HT$_{5A}$ serotonin receptor for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders. The *Journal of Psychiatric Research,* 38, 371-376 (2004) describes evidence for a potential significant role of the 5-HT$_{5A}$ gene in schizophrenia and more specifically in patients with later age at onset.

SUMMARY OF THE INVENTION

The present invention provides compounds of formula I

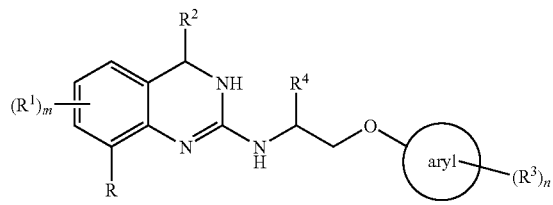

I wherein
R$^1$ is hydrogen, lower alkyl, lower alkoxy, halogen or lower alkyl substituted by halogen;
R is hydrogen or halogen; or
R$^1$ and R are together with the carbon atoms to which they are attached —CH=CH—CH=CH—;
R$^2$ is hydrogen, lower alkyl, phenyl optionally substituted by halogen, or is hetaryl optionally substituted by lower alkyl;
R$^3$ is hydrogen, lower alkyl, phenyl, benzyl, lower alkenyl, lower alkoxy, phenyloxy, benzyloxy, S-lower alkyl, halogen, CN, lower alkyl substituted by halogen or O-lower alkyl substituted by halogen;
R$^4$ is hydrogen or lower alkyl;
aryl is phenyl or naphthyl;
n is 1, 2 or 3; and
m is 1 or 2;

and pharmaceutically acceptable acid addition salts and tautomeric forms thereof.

The compounds of formula I can contain asymmetric carbon atoms. Accordingly, the present invention includes all stereoisomeric forms of the compounds of formula I, including each of the individual enantiomers and mixtures thereof.

The present invention also provides compositions containing one or more compounds of the invention and a pharmaceutically acceptable carrier. The invention further provides methods for preparing compounds and compositions of the invention.

Compounds of formula I have good activity on the 5-HT$_{5A}$ receptor. Therefore, the invention also provides methods for treating depression (which term includes bipolar depression, unipolar depression, single or recurrent major depressive episodes with or without psychotic features, catatonic features, melancholic features, atypical features or postpartum onset, seasonal affective disorders and dysthymia, depressive disorders resulting from a general medical condition including, but not limited to, myocardial infarction, diabetes, miscarriage or abortion), anxiety disorders, (which includes generalized anxiety and social anxiety disorder, schizophrenia, panic disorders, agoraphobia, social phobia, obsessive compulsive disorders, post-traumatic stress disorders, pain (particularly neuropathic pain), memory disorders (including dementia, amnesic disorders and age-associated memory impairment), disorders of eating behaviors (including nervosa and bulimia nervosa), sexual dysfunction, sleep disorders (including disturbances of circadian rhythm, dyssomnia, insomnia, sleep apnea and narcolepsy), withdrawal from abuse of drugs (such as of cocaine, ethanol, nicotine, benzodiazepines, alcohol, caffeine, phencyclidine and phencyclidine-like compounds, opiates such as cannabis, heroin, morphine, sedative hypnotic, amphetamine or amphetamine-related drugs), motor disorders such as Parkinson's disease, dementia in Parkinson's disease, neuroleptic-induced Parkinsonism and tardive dyskinesias, as well as other psychiatric disorders and gastrointestinal disorders such as irritable bowel syndrome (WO 2004/096771).

The preferred indications with regard to the present invention are the treatment of anxiety, depression, sleep disorders and schizophrenia.

DETAILED DESCRIPTION OF THE INVENTION

Unless otherwise stated, the following terms used in the present description have the definitions given herein. The definitions apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

The term "lower alkoxy" or "O-lower alkyl" denotes a group wherein the alkyl residues are as defined above and wherein the alkyl group is attached via an oxygen atom.

The term "S-lower alkyl" denotes a group wherein the alkyl residues are as defined above and wherein the alkyl group is attached via a sulfur atom.

The term "halogen" denotes chlorine, iodine, fluorine and bromine.

The term "lower alkyl substituted by halogen" denotes a lower alkyl group as defined above, wherein one or more hydrogen atoms have been replaced by (a) halogen atom(s), for example $CH_2F$, $CHF_2$, $CF_3$ or the like.

The term "O-lower alkyl substituted by halogen" denotes a lower alkyl group as defined above, wherein one or more hydrogen atoms have been replaced by (a) halogen atom(s) and wherein is attached via an oxygen atom for example $OCH_2F$, $OCHF_2$, $OCF_3$ or the like.

The term "lower alkenyl" denotes an alkyl residues as defined above, and wherein at least one carbon bond is a double bond.

The term "hetaryl" denotes a 5 or 6-membered heteroaryl ring, containing at least one N, O or S heteroatom, for example thiophenyl or isoxazolyl.

The term "thiophenyl" is synonymous with thienyl and denotes a 5-membered heteroaryl ring containing one sulfur atom as derived from thiophene.

The term "aryl" denotes a phenyl or naphthyl group, each of which can be unsubstituted or can be substituted with, for example, lower alkyl, lower alkenyl, lower alkoxy, benzyloxy, S-lower alkyl, halogen, CN, or O-lower alkyl substituted by halogen.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

The present invention provides compounds of formula I

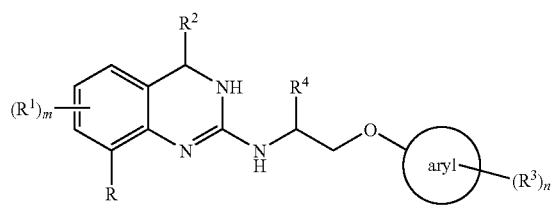

I wherein
$R^1$ is hydrogen, lower alkyl, lower alkoxy, halogen or lower alkyl substituted by halogen;
R is hydrogen or halogen; or
$R^1$ and R are together with the carbon atoms to which they are attached —CH=CH—CH=CH—;
$R^2$ is hydrogen, lower alkyl, phenyl optionally substituted by halogen, or is hetaryl optionally substituted by lower alkyl;
$R^3$ is hydrogen, lower alkyl, phenyl, benzyl, lower alkenyl, lower alkoxy, phenyloxy, benzyloxy, S-lower alkyl, halogen, CN, lower alkyl substituted by halogen or O-lower alkyl substituted by halogen;
$R^4$ is hydrogen or lower alkyl;
aryl is phenyl or naphthyl;
n is 1, 2 or 3; and
m is 1 or 2;

and pharmaceutically acceptable acid addition salts and tautomeric forms thereof.

The compounds of formula I can contain asymmetric carbon atoms. Accordingly, the present invention includes all stereoisomeric forms of the compounds of formula I, including each of the individual enantiomers and mixtures thereof.

Preferred compounds of formula I are those wherein aryl is phenyl, in particular unsubstituted phenyl.

Preferred compounds of formula I are those, wherein $R^2$ is hydrogen and aryl is unsubstituted phenyl ($R^3$ is hydrogen), for example the following compounds:
(6-fluoro-3,4-dihydro-quinazolin-2-yl)-(2-phenoxy-ethyl)-amine,
(6-methyl-3,4-dihydro-quinazolin-2-yl)-(2-phenoxy-ethyl)-amine,
(3,4-dihydro-quinazolin-2-yl)-(2-phenoxy-ethyl)-amine,
(5-fluoro-3,4-dihydro-quinazolin-2-yl)-(2-phenoxy-ethyl)-amine,
(5-chloro-3,4-dihydro-quinazolin-2-yl)-(2-phenoxy-ethyl)-amine,
(5-methyl-3,4-dihydro-quinazolin-2-yl)-(2-phenoxy-ethyl)-amine,
(5,6-dichloro-3,4-dihydro-quinazolin-2-yl)-(2-phenoxy-ethyl)-amine and
(6-methoxy-3,4-dihydro-quinazolin-2-yl)-(2-phenoxy-ethyl)-amine.

Preferred compounds of formula I wherein $R^2$ is hydrogen and aryl is unsubstituted phenyl further include those compounds wherein $R^1$ is hydrogen, in particular those wherein R, $R^1$, $R^2$, $R^3$, and $R^4$ all are hydrogen. Other such compounds are those wherein $R^1$ is halogen. Still other compounds within this group are those wherein $R^1$ is methyl. Also included in this group are compounds wherein $R^1$ is methoxy.

Other preferred compounds of formula I are those wherein $R^2$ is lower alkyl and aryl is unsubstituted phenyl, in particular, compounds of formula I, wherein $R^2$ is methyl and aryl is unsubstituted phenyl ($R^3$ is hydrogen), for example the following compound:
(4-methyl-3,4-dihydro-quinazolin-2-yl)-(2-phenoxy-ethyl)-amine.

Other preferred compounds of formula I are those wherein $R^2$ is hetaryl optionally substituted by lower alkyl and aryl is unsubstituted phenyl. Particularly preferred within this group are compounds wherein $R^2$ is a thiophenyl. Also preferred are such compounds wherein $R^2$ is an isoxazolyl.

Preferred compounds of formula I are those wherein $R^2$ is phenyl optionally substituted by halogen; compounds wherein phenyl is substituted with one or more halogen is preferred.

Preferred compounds of formula I are those wherein aryl is substituted phenyl. Among such compounds are those wherein R² is phenyl optionally substituted by halogen. Also in this group are preferred compounds wherein R¹ is methoxy. Other such compounds are those wherein R¹ is halogen. Still further preferred compounds within this group are those wherein R¹ is methyl. Preferred compounds are those within this group wherein R, R¹, R², R³, and R⁴ all are hydrogen. Also preferred are compounds in which n is 2.

Further preferred are compounds, wherein R² is hydrogen and aryl is phenyl, substituted by lower alkyl, lower alkenyl, lower alkoxy, benzyloxy, S-lower alkyl, halogen, CN, or O-lower alkyl substituted by halogen, for example the following compounds:

(3,4-dihydro-quinazolin-2-yl)-[2-(2-methoxy-phenoxy)-ethyl]-amine,
[2-(2-chloro-phenoxy)-ethyl]-(3,4-dihydro-quinazolin-2-yl)-amine,
(3,4-dihydro-quinazolin-2-yl)-[2-(2-fluoro-phenoxy)-ethyl]-amine,
(3,4-dihydro-quinazolin-2-yl)-[2-(2-ethoxy-phenoxy)-ethyl]-amine,
(3,4-dihydro-quinazolin-2-yl)-(2-m-tolyloxy-ethyl)-amine,
(3,4-dihydro-quinazolin-2-yl)-[2-(2-trifluoromethoxy-phenoxy)-ethyl]-amine,
(3,4-dihydro-quinazolin-2-yl)-[2-(3-methoxy-phenoxy)-ethyl]-amine,
(3,4-dihydro-quinazolin-2-yl)-[2-(3-fluoro-phenoxy)-ethyl]-amine,
[2-(3-chloro-phenoxy)-ethyl]-(3,4-dihydro-quinazolin-2-yl)-amine,
(6-fluoro-3,4-dihydro-quinazolin-2-yl)-[2-(2-methoxy-phenoxy)-ethyl]-amine,
(3,4-dihydro-quinazolin-2-yl)-[2-(2-propenyl-phenoxy)-ethyl]-amine,
(3,4-dihydro-quinazolin-2-yl)-[2-(2-methylsulfanyl-phenoxy)-ethyl]-amine,
[2-(2-bromo-phenoxy)-ethyl]-(3,4-dihydro-quinazolin-2-yl)-amine,
2-[2-(3,4-dihydro-quinazolin-2-ylamino)-ethoxy]-benzonitrile,
[2-(2-benzyloxy-phenoxy)-ethyl]-(3,4-dihydro-quinazolin-2-yl)-amine,
(3,4-dihydro-quinazolin-2-yl)-[2-(2,6-dimethoxy-phenoxy)-ethyl]-amine,
(3,4-dihydro-quinazolin-2-yl)-[2-(2-methoxy-5-methyl-phenoxy)-ethyl]-amine,
(3,4-dihydro-quinazolin-2-yl)-[2-(2-fluoro-6-methoxy-phenoxy)-ethyl]-amine,
[2-(2-bromo-5-fluoro-phenoxy)-ethyl]-(3,4-dihydro-quinazolin-2-yl)-amine,
[2-(2-chloro-phenoxy)-ethyl]-(6-methoxy-3,4-dihydro-quinazolin-2-yl)-amine,
[2-(2-chloro-phenoxy)-ethyl]-(6-methyl-3,4-dihydro-quinazolin-2-yl)-amine,
[2-(2-chloro-phenoxy)-ethyl]-(5-fluoro-3,4-dihydro-quinazolin-2-yl)-amine,
(6-methoxy-3,4-dihydro-quinazolin-2-yl)-[2-(2-methoxy-phenoxy)-ethyl]-amine,
[2-(2-methoxy-phenoxy)-ethyl]-(6-methyl-3,4-dihydro-quinazolin-2-yl)-amine and
(5-fluoro-3,4-dihydro-quinazolin-2-yl)-[2-(2-methoxy-phenoxy)-ethyl]-amine.

Other preferred compounds of formula I are those wherein aryl is naphthyl, in particular those compounds in which R, R¹, R², R³, and R⁴ all are hydrogen.

Preferred compounds of formula I are those wherein R1 and R are together with the carbon atoms to which they are attached —CH=CH—CH=CH—.

Preferred compounds of formula I also are those in which R¹ is lower alkyl, lower alkoxy, halogen, or lower alkyl substituted by halogen. For example, compounds wherein R¹ is lower alkyl are preferred. Also preferred are compounds wherein R¹ is lower alkyl substituted by lower alkyl substituted by halogen. Still other preferred compounds are those of formula I wherein R¹ is lower alkoxy. Other preferred compounds are those wherein R¹ is halogen.

The present compounds of formula I and their pharmaceutically acceptable salts can be prepared by methods known in the art, for example by processes described below, which process comprises reacting a compound of formula

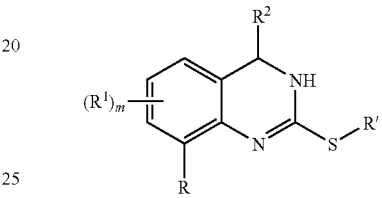

VIII with a compound of formula

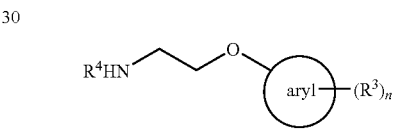

to obtain a compound of formula

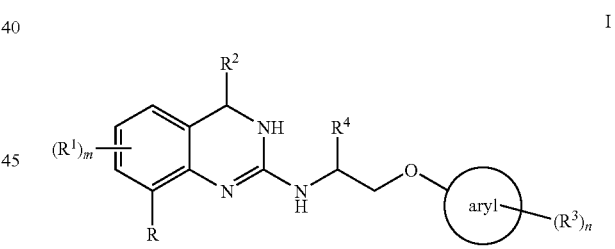

I wherein R¹, R², R³, R⁴, n and aryl are as described above, and R' is alkyl, such as methyl, and if desired, converting the compounds obtained into pharmaceutically acceptable acid addition salts.

An 2-alkylsulfanyl-3,4-dihydro-quinazoline of formula VIII is heated with a (substituted) 2-aryloxyethylamine in a suitable solvent, such as acetonitril. (3,4-Dihydro-quinazolin-2-yl)-(2-phenoxy-ethyl)-amine of formula I can then be isolated from the reaction mixture by conventional purification.

In examples 1-68 and in the following scheme 1 the preparation of compounds of formula I is described in more detail. The starting materials are known compounds or can be prepared according to methods known in the art.

Compounds of formula I can be prepared in accordance with the following scheme 1:

Scheme 1

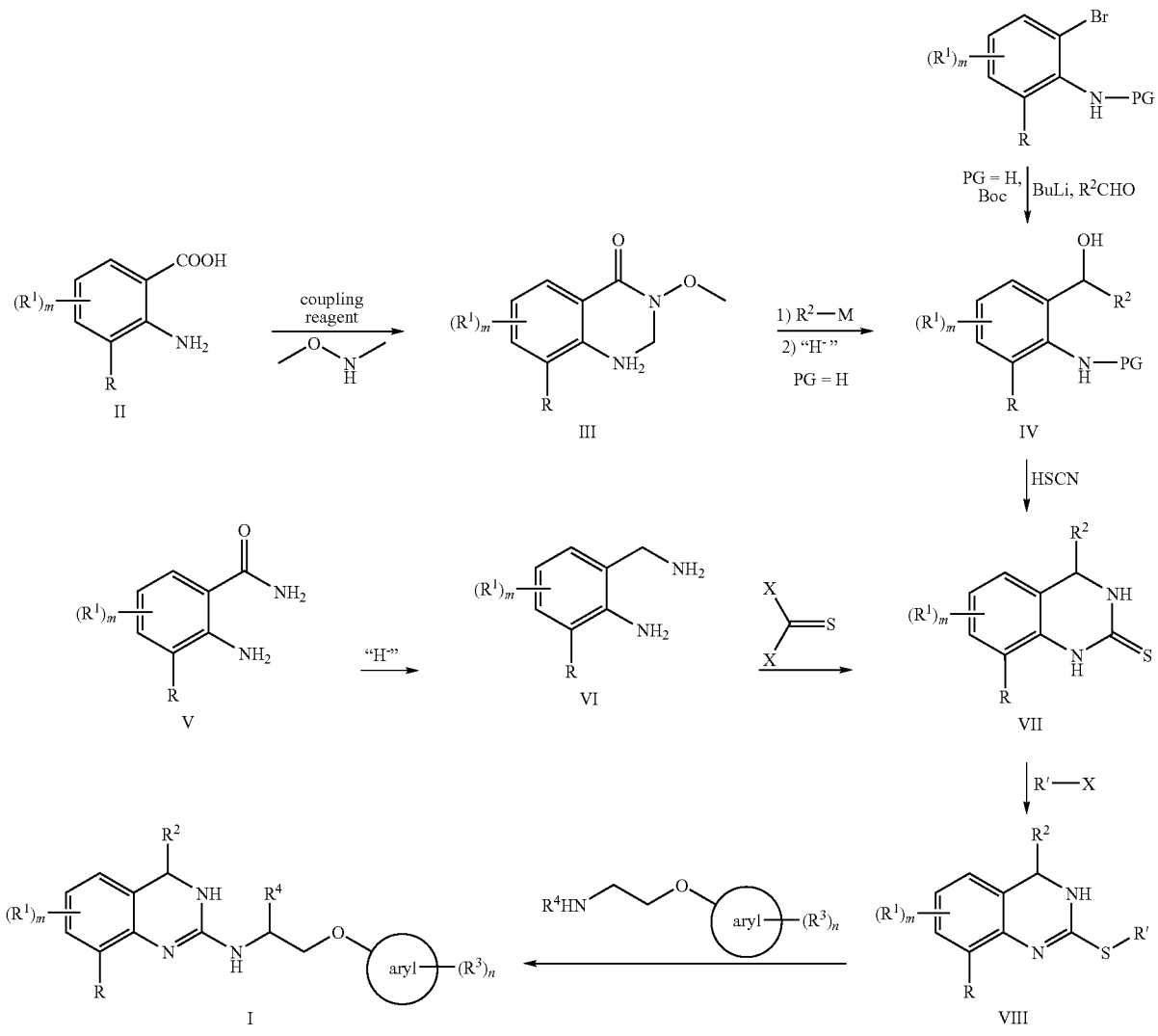

R²—M = metallo-organic reagent
X = leaving group
PG = protecting group
R = alkyl A 3,4-dihydro-1H-quinazoline-2-thione VII is reacted with an alkylating agent R—X, such as methyl iodide, in a suitable solvent, such as acetone, to give an 2-alkylsulfanyl-3,4-dihydro-quinazoline VIII, which can be isolated from the reaction mixture by conventional methods, for instance filtration. VIII is then heated with a (substituted) 2-phenoxyethylamine in a suitable solvent, such as acetonitril. (3,4-Dihydro-quinazolin-2-yl)-(2-phenoxy-ethyl)-amine I can then be isolated from the reaction mixture by conventional purification.

3,4-Dihydro-1H-quinazoline-2-thiones VII can be prepared by several methods. In one such method, a 2-aminobenzamide V is reacted with a hydride transfer reagent, such as LiAlH₄, in a suitable solvent, such as THF. Elevated temperature might be required to carry out the reaction. After hydrolysis of excess reagent, 2-aminomethyl-phenylamine VI is isolated from the mixture by conventional workup and purification. VI can then be reacted with thiophosgene, or a thiophosgene equivalent, in a suitable solvent, such as diethyl ether. A base, such as triethylamine, can be added to the reaction mixture to neutralize acidic by-products. After the evaporation of the solvent, the crude product can be used usually without further purification in the next step.

Another method to obtain 3,4-dihydro-1H-quinazoline-2-thiones VII is as follows: an anthranilic acid II is suitably activated, for instance with a coupling reagent such as HBTU, and converted with N,O-dimethylhydroxylamine in a suitable solvent, such as DMF, and optionally in the presence of a base, such as NMM, to a Weinreb amide of formula III. After isolation and purification by conventional means, III is then converted with a metalloorganic reagent R²—M, such as alkyllithium, in a suitable solvent, such as THF, for instance by allowing the reaction mixture to warm from low temperature, e.g. −78° C., to room temperature. Conventional workup and purification then gives a phenylalkanone, which can be converted to the corresponding phenylalkanole IV. Alternatively the phenylalkanole IV can be prepared from the corresponding 2-bromo-aniline or its mono-boc-protected derivative, which can be prepared by direct mono-boc-protection or via bis-boc-protection and selective mono-deprotection, by metal-halogen exchange with for example butyl lithium, eventual through prior deprotonation with a base, for instance phenyl magenesium chloride, and quenching with an aldehyde at low to room temperature. The phenylalkanole IV can be converted to 3,4-dihydro-1H-quinazoline-2-thione VII with HSCN, which might be generated in situ from thiocyanate salt, e.g. KSCN, and an acid, e.g. HCl. Elevated temperature is usually necessary to carry out the reaction. VII can then be obtained by conventional workup and purification of the reaction mixture. The latter two steps to the 3,4-dihydro-1H-quinazoline-2-thione VII can be also performed in one step without isolation of the intermediates.

The following abbreviations have been used:
HBTU=O-benzotriazol-1-yl-N,N,N',N'-tetramethyluronium hexafluorophosphate
DMF=N,N-dimethylformamide
NMM=N-methylmorpholine
THF=tetrahydrofuran Compounds of the invention were tested for 5-HT$_{5A}$ activity in the following assay.

Test Description

A [$^3$H]LSD radioligand binding assay was used to determine the affinity of the compounds for the recombinant human 5-HT$_{5A}$ receptor, in membranes from transiently (cDNA) expressed 5-HT$_{5A}$ receptors in Human Embryonic Kidney-EBNA (HEK-EBNA) cells. Assay buffer consisted of Tris (50 mM) buffer containing 1 mM EGTA, 10 mM MgCl$_2$ (pH 7.4) and 10 µM pargyline. The binding assay was carried out in 96-well-plates in the presence of [$^3$H]LSD (approximately 1 nM), approximately 2 µg/well of membrane protein, and 0.5 mg of Ysi-poly-l-lysine SPA beads in a final volume of 200 µl of buffer. Non-specific binding was defined using methiothepin 2 µM. Compounds were tested at 10 concentrations. All assays were conducted in duplicate and repeated at least two times. Assay plates were incubated for 120 min at room temperature before centrifugation. Bound ligand was determined using a Packard Topcount scintillation counter. IC$_{50}$ values were calculated using a non-linear curve fitting program and Ki values calated using the Cheng-Prussoff equation.

The activity of the present preferred compounds (≦100 nM) is described in the table below:

| Example | Ki (nM) |
|---------|---------|
| 1 | 7.5 |
| 2 | 18 |
| 3 | 19 |
| 4 | 25 |
| 5 | 42 |
| 6 | 34 |
| 7 | 30 |
| 8 | 38 |
| 9 | 53 |
| 10 | 46 |
| 11 | 58 |
| 12 | 64 |
| 13 | 72 |
| 14 | 76 |
| 15 | 76 |
| 16 | 96 |
| 17 | 96 |
| 18 | 100 |

-continued

| Example | Ki (nM) |
|---------|---------|
| 29 | 19.9 |
| 34 | 58.7 |
| 35 | 35.7 |
| 37 | 22.2 |
| 38 | 54.0 |
| 39 | 86.7 |
| 41 | 90.3 |
| 44 | 82.5 |
| 45 | 42.9 |
| 46 | 89.0 |
| 56 | 83.1 |
| 58 | 53.8 |
| 59 | 48.4 |
| 62 | 53.6 |
| 64 | 19.7 |
| 67 | 23.6 |

The present invention also provides pharmaceutical compositions containing compounds of formula I or a pharmaceutically acceptable salt thereof and a pharmaceutically acceptable carrier. Such pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, parenterally, e.g., in the form of injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like.

Suitable carriers for suppositories are, for example, natural or hardened oils, waxes, fats, semi-liquid or liquid polyols and the like.

The pharmaceutical compositions also can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing one or more compounds of formula I and/or pharmaceutically acceptable acid addition salts and, if desired, one or more other therapeutically valuable substances into a galenical administration form together with one or more therapeutically inert carriers.

As mentioned earlier, the compounds of formula I and their pharmaceutically acceptable addition salts possess valuable pharmaceutical properties. Compounds of the present invention are active on the 5-HT$_{5A}$ receptor and therefore suitable for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

The most preferred indications in accordance with the present invention are those, which include disorders of the central nervous system, for example the treatment of anxiety, depression, sleep disorders and schizophrenia.

The dosage at which the compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| | Tablet Formulation (Wet Granulation) mg/tablet | | | |
|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granulates at 50° C.
3. Pass the granules through suitable milling equipment.
4. Add item 5 and mix for three minutes; compress on a suitable press.

| | Capsule Formulation | | | |
|---|---|---|---|---|
| | | mg/capsule | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

Compounds of formula I can be prepared as shown in the following description:

EXAMPLE 1

(3,4-Dihydro-quinazolin-2-yl)-[2-(2-methoxy-phenoxy)-ethyl]-amine

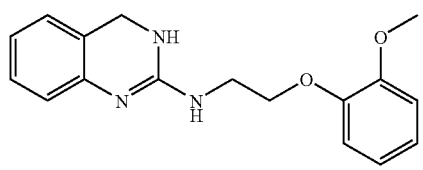

a) [2-(2-Methoxy-phenoxy)-ethyl]-carbamic acid tert-butyl ester

Under an atmosphere of nitrogen, (2-hydroxy-ethyl)-carbamic acid tert-butyl ester (584 mg, 3.62 mmol) and triphenylphosphine (951 mg, 3.63 mmol) were added to a solution of ortho-methoxyphenol (500 mg, 4.03 mmol) in THF (8 ml). Subsequently, diethyl azodicarboxylate (772 mg, 4.44 mmol) was added at 0° C. and the reaction mixture was then stirred for 3 h at r.t. The solvent was evaporated under reduced pressure, the residue was taken up in ethyl acetate, washed ($H_2O$), and dried ($Na_2SO_4$). Chromatographic purification gave the title compound (320 mg, 30%).

$^1$H NMR (CDCl$_3$): δ 1.45 (9H, s), 3.53 (2H, t), 3.87 (3H, s), 4.08 (2H, t), 5.23 (1H, bs), 6.89-6.96 (4H, m).

b) 2-(2-Methoxy-phenoxy)-ethylamine

Under an atmosphere of Nitrogen, 3N HCl (3 ml) was added to a solution of [2-(2-methoxy-phenoxy)-ethyl]-carbamic acid tert-butyl ester (320 mg, 1.20 mmol) in dioxane (3 ml). The mixture was heated to reflux (2 h). Upon cooling, the reaction mixture was taken up in ethyl acetate, and extracted several times with $H_2O$. The combined $H_2O$ extracts were then made alkaline by addition of NaOH 2N, and extracted with ethyl acetate. The ethyl acetate extract was dried ($Na_2SO_4$), and the solvent was evaporated. The obtained product (180 mg, 90%) was used in the next step without further purification.

$^1$H NMR (CDCl$_3$): δ 1.65 (2H, bs), 3.11 (2H, t), 3.86 (3H, s), 4.05 (2H, t), 6.88-6.94 (4H, m).

c) 2-Methylsulfanyl-3,4-dihydro-quinazoline hydroiodide

Under a atmosphere of nitrogen, a solution of thiophosgene in diethyl ether was slowly added at −78° C. to a mixture of 2-aminobenzylamine, triethylamine and diethyl ether. After being kept at −78° for an additional 15 min, the reaction mixture was allowed to warm to r.t. The precipitate was filtered, washed with diethyl ether, and dissolved in MeOH. To this solution, KOH was added, the precipitated KCl was removed by filtration, and the filtrate was evaporated under reduced pressure. The obtained product (7.55 g, 70%) was used for the next step without further purification.

Methyl iodide (11.5 ml, 184 mmol) was added to a solution of 3,4-dihydro-1H-quinazoline-2-thione (7.55 g, 46 mmol) in ethanol (150 ml), and the mixture was heated to reflux (3.5 h). The majority of the solvent was then evaporated under reduced pressure, and the precipitate was collected by filtration and washed with a small amount of cold ethanol. The thus obtained title compound (9.60 g, 68%) was used in the next step without further purification.

$^1$H NMR (d$^6$-DMSO): δ 2.74 (3H, s), 4.72 (2H, s), 7.06 (1H, d), 7.24 (2H, m), 7.35 (1H, m).

d) (3,4-Dihydro-quinazolin-2-yl)-[2-(2-methoxy-phenoxy)-ethyl]-amine 2-(2-Methoxy-phenoxy)-ethylamine (42 mg, 0.25 mmol) was added to a solution of 2-methylsulfanyl-3,4-dihydro-quinazoline hydroiodide (70 mg, 0.23 mmol) in acetonitrile (1 ml), and the mixture was heated overnight (80° C.) in a screw-capped vial. The title compound (42 mg, 62%) was then isolated from the reaction mixture by preparative, reverse-phase HPLC (YMC CombiPrep C18 column 50×20 mm, solvent gradient 5-95% CH$_3$CN in 0.1% TFA(aq) over 6.0 min, λ=230 nm, flow rate 40 ml/min).

MS: m/e=298.2 [M+H$^+$]. $^1$H NMR (CDCl$_3$): δ 3.71 (3H, s), 3.91 (2H, t), 4.16 (2H, t), 4.57 (2H, s), 6.85-7.01 (8H, m), 7.80 (1H, bs), 8.63 (1H, s).

EXAMPLE 2

(6-Fluoro-3,4-dihydro-quinazolin-2-yl)-(2-phenoxy-ethyl)-amine

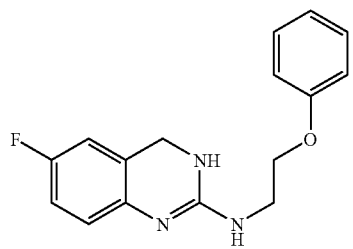

The title compound (MS: m/e=286.1 [M+H$^+$]) was prepared in analogy to example 1 from 2-phenoxyethylamine and 2-aminomethyl-4-fluoro-phenylamine.

EXAMPLE 3

[2-(2-Chloro-phenoxy)-ethyl]-(3,4-dihydro-quinazolin-2-yl)-amine

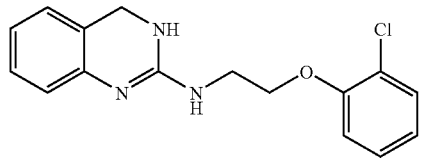

The title compound (MS: m/e=302.1 [M+H$^+$]) was prepared in analogy to example 1 from 2-chlorophenol.

$^1$H NMR (CDCl$_3$): δ 3.80 (2H, t), 4.24 (2H, t), 4.61 (2H, s), 6.92-7.16 (4H, m), 7.23-7.30 (3H, m), 7.41 (1H, m), 8.69 (1H, s), 10.40 (1H, s).

EXAMPLE 4

(6-Methyl-3,4-dihydro-quinazolin-2-yl)-(2-phenoxy-ethyl)-amine

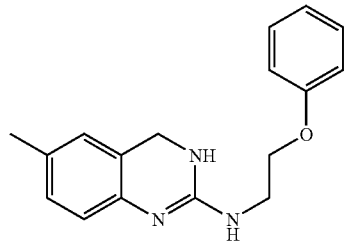

a) 2-Aminomethyl-4-methyl-phenylamine

Under an atmosphere of argon, a solution 2-amino-5-methylbenzamide (1.2 g, 80 mmol) in THF (25 ml) was added to a suspension of LiAlH$_4$ (1.54 g, 40 mmol) in THF (25 ml) over 20 min. The suspension was heated to reflux (4 h). For workup, the mixture was cooled to 0° C., and 1.5 ml H$_2$O, 3 ml 4n NaOH, and 3 ml H$_2$O were added subsequently. The suspension was dried (Na$_2$SO$_4$), and evaporated under reduced pressure. The title compound (700 mg, 63%) was isolated from the residue by chromatographic purification (silica gel, CH$_2$Cl$_2$/MeOH (2M NH$_3$)=9:1).

MS: m/e=136 [M$^+$]. $^1$H NMR (CDCl$_3$): δ 2.23 (3H, s), 3.86 (2H, s), 6.61 (1H, d), 6.88 (2H, m).

b) (6-Methyl-3,4-dihydro-quinazolin-2-yl)-(2-phenoxy-ethyl)-amine

The title compound (MS: m/e=282.4 [M+H$^+$]) was prepared in analogy to example 1 from 2-phenoxyethylamine and 2-aminomethyl-4-methyl-phenylamine.

EXAMPLE 5

(3,4-Dihydro-quinazolin-2-yl)-(2-phenoxy-ethyl)-amine hydroiodide

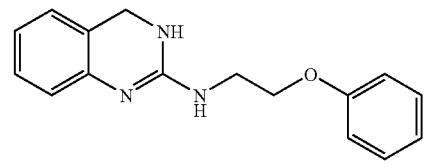

2-Phenoxyethylamine (21 mg, 0.16 mmol) was added to a solution of 2-methylsulfanyl-3,4-dihydro-quinazoline hydroiodide (50 mg, 0.16 mmol, prepared as under example 1 [c]) in acetonitrile (1 ml), and the mixture was heated overnight (80° C.) in a screw-capped vial. The solvent was then evaporated and the mixture was suspended in diethyl ether. The title compound (41 mg, 95%) was obtained from this mixture by filtration.

MS: m/e=268.3 [M+H$^+$]

EXAMPLE 6

(3,4-Dihydro-quinazolin-2-yl)-[2-(2-fluoro-phenoxy)-ethyl]-amine

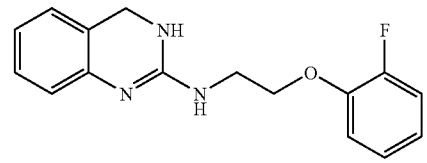

The title compound (MS: m/e=286.0 [M+H$^+$]) was prepared in analogy to example 1 from 2-fluorophenol.

EXAMPLE 7

(5-Fluoro-3,4-dihydro-quinazolin-2-yl)-(2-phenoxy-ethyl)-amine hydroiodide

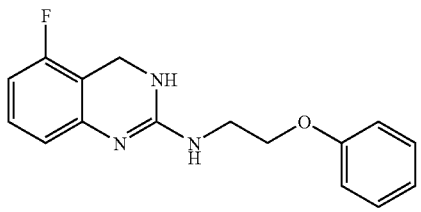

The title compound (MS: m/e=286.1 [M+H$^+$]) was prepared in analogy to example 5 from 2-aminomethyl-3-fluoro-phenylamine.

$^1$H NMR (d$^6$-DMSO): δ 3.69 (2H, t), 4.16 (2H, t), 4.54 (2H, s), 6.88-7.00 (5H, m), 7.28-7.36 (3H, m).

EXAMPLE 8

(3,4-Dihydro-quinazolin-2-yl)-[2-(2-ethoxy-phenoxy)-ethyl]-amine

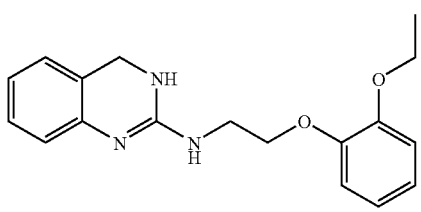

The title compound (MS: m/e=311.9 [M+H$^+$]) was prepared in analogy to example 1 from 2-ethoxyphenol.

$^1$H NMR (CDCl$_3$): δ 1.44 (m, 3H), 3.72 (2H, t), 4.16 (4H, m), 4.56 (2H, s), 6.87-7.03 (4H, m), 7.21-7.30 (4H, m), 8.73 (1H, s), 11.20 (1H, s).

EXAMPLE 9

(5-Chloro-3,4-dihydro-quinazolin-2-yl)-(2-phenoxy-ethyl)-amine hydroiodide

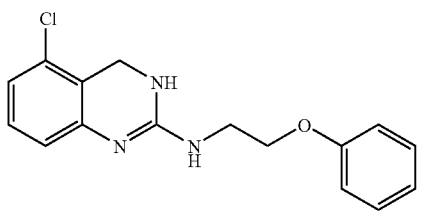

The title compound (MS: m/e=302.1 [M+H$^+$]) was prepared in analogy to example 5 from 2-phenoxyethylamine and 2-aminomethyl-3-chloro-phenylamine.

$^1$H NMR (d$^6$-DMSO): δ 3.70 (2H, t), 4.15 (2H, t), 4.54 (2H, s), 6.94-7.05 (5H, m), 7.20-7.36 (3H, m).

EXAMPLE 10

(5-Methyl-3,4-dihydro-quinazolin-2-yl)-(2-phenoxy-ethyl)-amine hydroiodide

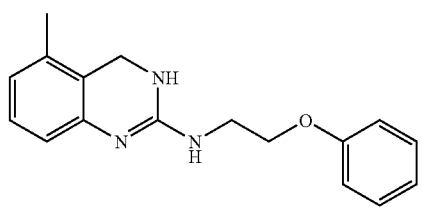

The title compound (MS: m/e=282.3 [M+H$^+$]) was prepared in analogy to example 5 from 2-phenoxyethylamine and 2-aminomethyl-3-methyl-phenylamine.

$^1$H NMR (d$^6$-DMSO): δ 3.70 (2H, t), 4.14 (2H, t), 4.48 (2H, s), 6.87-6.99 (5H, m), 7.14-7.34 (3H, m), 7.88 (1H, bs), 8.42 (1H, bs), 10.13 (1H, bs).

EXAMPLE 11

(4-Methyl-3,4-dihydro-quinazolin-2-yl)-(2-phenoxy-ethyl)-amine hydroiodide

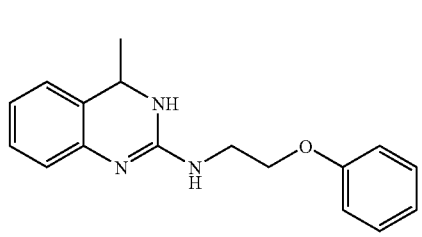

a) 4-Methyl-3,4-dihydro-1H-quinazoline-2-thione

At a temperature of 65° C., sodium borohydride (281 mg, 4.4 mmol) was added to a solution of 2-aminoacetophenone (1.00 g, 7.4 mmol) in ethanol (6 ml). The mixture was stirred overnight (65° C.). At r.t., H$_2$O (1.5 ml), a solution of potassium thiocyanate (800 mg in 1.5 ml H$_2$O, 8.2 mmol) and HCl (1.5 ml HCl conc in 2 ml H$_2$O) were added subsequently. The mixture was then stirred for 3 h at 65° C. The solvent was evaporated under reduced pressure, the residue was taken up in ethyl acetate and washed with water. After drying (Na$_2$SO$_4$) and evaporation of the solvent, the residue was recrystallized from isopropanol to give the title compound (410 mg, 31%).

$^1$H NMR (d$^6$-DMSO): δ 1.32 (3H, d), 4.55 (1H, q), 6.93-7.00 (2H, m), 7.12-7.19 (2H, m), 8.71 (1H, bs), 10.43 (1H, bs).

b) 4-Methyl-2-methylsulfanyl-3,4-dihydro-quinazoline hydroiodide

Methyl iodide (0.43 ml, 6.94 mmol) was added to a solution of 4-methyl-3,4-dihydro-1H-quinazoline-2-thione (410 mg, 2.30 mmol) in acetone (5 ml). The mixture was stirred for 15 min (r.t.), and the title compound (500 mg, 67%) was isolated from the reaction mixture by filtration.

$^1$H NMR (d$^6$-DMSO): δ 1.46 (3H, d), 2.76 (3H, s), 5.02 (1H, q), 7.11 (1H, d), 7.27-7.39 (3H, m), 10.25 (1H, bs), 12.03 (1H, bs).

c) (4-Methyl-3,4-dihydro-quinazolin-2-yl)-(2-phenoxy-ethyl)-amine hydroiodide 2-Phenoxyethylamine (26 mg, 0.19 mmol) was added to a solution of 4-methyl-2-methylsulfanyl-3,4-dihydro-quinazoline hydroiodide (50 mg, 0.16 mmol) in acetonitrile (1 ml), and the mixture was heated overnight (80° C.) in a screw-capped vial. The solvent was then evaporated and the mixture was suspended in diethyl ether. The title compound (52 mg, 62%) was obtained from this mixture by filtration.

MS: m/e=282.1 [M+H$^+$]. $^1$H NMR (CDCl$_3$): δ 1.40 (3H, d), 3.72 (2H, m), 4.14 (2H, m), 4.80 (2H, q), 6.94-7.07 (3H, m), 7.11-7.16 (2H, m), 7.26-7.34 (4H, m), 7.89 (1H, bs), 8.56 (1H, bs), 10.25 (1H, bs).

EXAMPLE 12

(3,4-Dihydro-quinazolin-2-yl)-(2-m-tolyloxy-ethyl)-amine

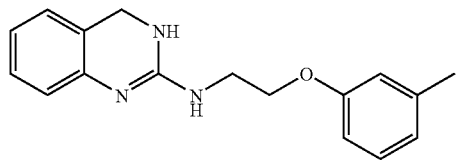

The title compound (MS: m/e 282.1 [M+H$^+$]) was prepared in analogy to example 1 from 3-methylphenol.

$^1$H NMR (CDCl$_3$): δ 2.33 (3H, s), 3.71 (2H, t), 4.17 (2H, t), 4.59 (2H, s), 6.67 (1H, d), 6.69 (1H, s), 6.85 (1H, d), 7.05-7.09 (3H, m), 7.19 (1H, dd), 7.25 (1H, m), 8.66 (1H, s), 10.80 (1H, s).

EXAMPLE 13

(3,4-Dihydro-quinazolin-2-yl)-[2-(2-trifluoromethoxy-phenoxy)-ethyl]-amine

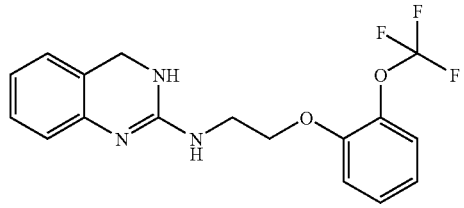

The title compound (MS: m/e=352.1 [M+H$^+$]) was prepared in analogy to example 1 from 2-trifluoromethoxy-phenol.

$^1$H NMR (CDCl$_3$): δ 3.76 (2H, t), 4.23 (2H, t), 4.58 (2H, s), 6.99-7.14 (4H, m), 7.21-7.31 (4H, m), 8.70 (1H, s), 10.80 (1H, s).

EXAMPLE 14

(5,6-Dichloro-3,4-dihydro-quinazolin-2-yl)-(2-phenoxy-ethyl)-amine hydroiodide

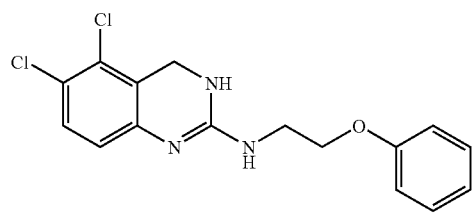

The title compound (MS: m/e=336.3 [M+H$^+$]) was prepared in analogy to example 5 from 2-phenoxyethylamine and 2-aminomethyl-3,4-dichloro-phenylamine.

$^1$H NMR (d$^6$-DMSO): δ 3.69 (2H, t), 4.14 (2H, t), 4.57 (2H, s), 6.94-7.08 (4H, m), 7.29-7.36 (2H, m), 7.55-7.58 (1H, m), 8.15 (3H, bs).

EXAMPLE 15

(6-Methoxy-3,4-dihydro-quinazolin-2-yl)-(2-phenoxy-ethyl)-amine

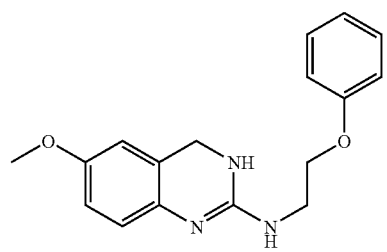

The title compound (MS: m/e 298.5 [M+H$^+$]) was prepared in analogy to example 1 from 2-phenoxyethylamine and 2-aminomethyl-4-methoxy-phenylamine. 6-Methoxy-3,4-dihydro-1H-quinazoline-2-thione was prepared by the method of Manetsch, Roman; Zheng, Lei; Reymond, Martine T.; Woggon, Wolf-Dietrich; Reymond, Jean-Louis *Chemistry—A European Journal* 2004, 10(10), 2487-2506.

EXAMPLE 16

(3,4-Dihydro-quinazolin-2-yl)-[2-(3-methoxy-phenoxy)-ethyl]-amine

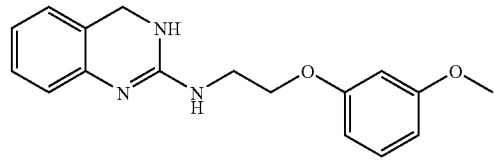

The title compound (MS: m/e=298.2 [M+H$^+$]) was prepared in analogy to example 1 from 3-methoxyphenol.

¹H NMR (CDCl₃): δ 3.74 (2H, t), 3.78 (3H, s), 4.16 (2H, t), 4.59 (2H, s), 6.43 (1H, m), 6.46 (1H, d), 6.58 (1H, d), 7.06-7.10 (3H, m), 7.20 (1H, dd), 7.22 (1H, m), 8.66 (1H, s), 10.00 (1H, s).

EXAMPLE 17

(3,4-Dihydro-quinazolin-2-yl)-[2-(3-fluoro-phenoxy)-ethyl]-amine

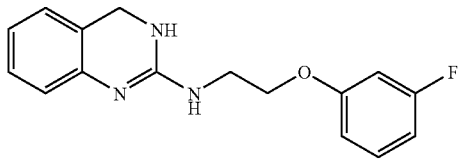

The title compound (MS: m/e=286.0 [M+H⁺]) was prepared in analogy to example 1 from 3-fluorophenol.

EXAMPLE 18

[2-(3-Chloro-phenoxy)-ethyl]-(3,4-dihydro-quinazolin-2-yl)-amine

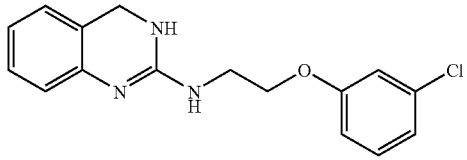

The tide compound (MS: m/e=302.2 [M+H⁺]) was prepared in analogy to example 1 from 3-chlorophenol.

EXAMPLE 19

(3,4-Dihydro-quinazolin-2-yl)-(2-o-tolyloxy-ethyl)-amine

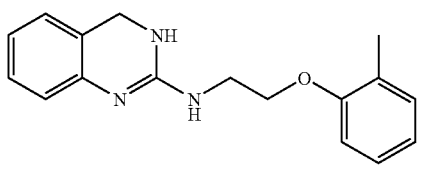

The title compound (MS: m/e=282.1 [M+H⁺]) was prepared in analogy to example 1 from 2-methylphenol.

EXAMPLE 20

(3,4-Dihydro-quinazolin-2-yl)-[2-(4-fluoro-phenoxy)-ethyl]-amine

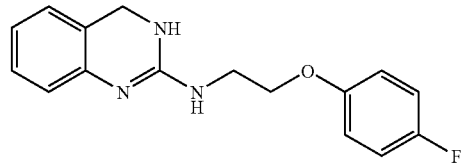

The title compound (MS: m/e=286.2 [M+H⁺]) was prepared in analogy to example 1 from 4-fluorophenol.

¹H NMR (CDCl₃): δ 3.68 (2H, m), 4.14 (2H, m), 4.50 (2H, s), 6.43 (1H, m), 6.86-7.31 (9H, m), 7.99 (1H, bs), 8.50 (1H, bs).

EXAMPLE 21

(7-Chloro-3,4-dihydro-quinazolin-2-yl)-(2-phenoxy-ethyl)-amine

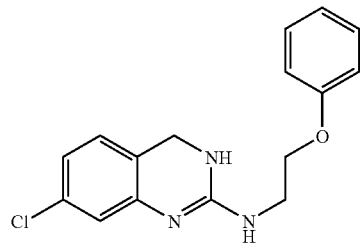

The title compound (MS: m/e=302.1 [M+H⁺]) was prepared in analogy to example 1 from 2-phenoxyethylamine and 2-aminomethyl-5-chloro-phenylamine.

EXAMPLE 22

(3,4-Dihydro-quinazolin-2-yl)-[2-(naphthalen-2-yloxy)-ethyl]-amine

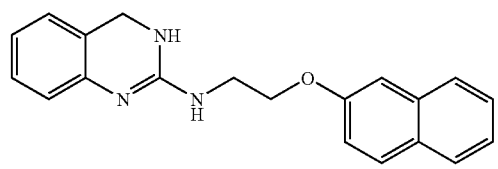

The title compound (MS: m/e=318.2 [M+H⁺]) was prepared in analogy to example 1 from naphtalene-2-ol.

EXAMPLE 23

[2-(4-Chloro-phenoxy)-ethyl]-(3,4-dihydro-quinazolin-2-yl)-amine hydroiodide

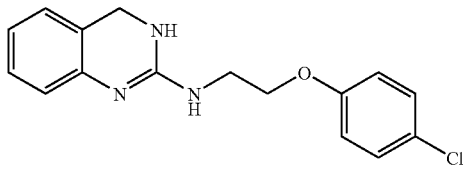

The title compound (MS: m/e=302.2 [M+H$^+$]) was prepared in analogy to example 5 from 4-chlorophenol.

EXAMPLE 24

(3,4-Dihydro-quinazolin-2-yl)-(2-p-tolyloxy-ethyl)-amine

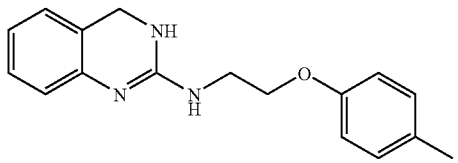

The title compound (MS: m/e=282.1 [M+H$^+$]) was prepared in analogy to example 1 from 4-methylphenol.
$^1$H NMR (CDCl$_3$): δ 2.28 (3H, s), 3.72 (2H, t), 4.15 (2H, t), 4.59 (2H, s), 6.77 (2H, d), 7.04-7.11 (5H, m), 7.23-7.26 (1H, m), 8.70 (1H, s), 10.30 (1H, s).

EXAMPLE 25

(8-Bromo-6-chloro-4-methyl-3,4-dihydro-quinazolin-2-yl)-(2-phenoxy-ethyl)-amine

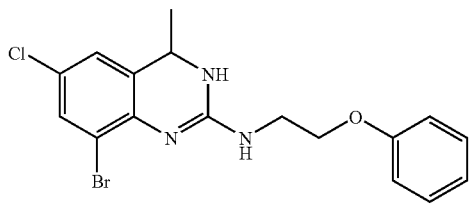

a) 1-(2-Amino-3-bromo-5-chloro-phenyl)-ethanol

At –78° C. under nitrogen 1.8 M phenyl magnesium chloride solution in THF (3.06 ml, 5.5 mmol) were added dropwise to 2,6-dibromo-4-chloroaniline (1.426 g, 5.0 mmol) in THF (25 ml). The clear solution was warmed to –20° C. and stirred at this temperature for 5 minutes. The clear yellow solution was cooled to –78° C. and 1.6 M n-butyllithium solution in hexane (6.25 ml, 10 mmol) was added dropwise. The reaction was warmed to –10° C. and again cooled to –78° C. at which temperature acetaldehyde (440 mg, 10 mmol) dissolved in THF (5 ml) was added. After stirring for 10 minutes at –78° C. 1N aqueous hydrogen chloride solution was added and the reaction was allowed to warm to room temperature. The reaction was extracted twice with diethyl ether, dried over sodium sulfate, filtered and the solvent was evaporated to yield the product as a mixture of the corresponding amine, imine and aminal. The crude product was used directly in the next step.

b) 8-Bromo-6-chloro-4-methyl-3,4-dihydro-1H-quinazoline-2-thione

The crude mixture of the previous step was suspended in a mixture of ethanol (4 ml), water (6 ml) and aqueous concentrated hydrogen chloride solution (1.5 ml). Potassium thiocyanate (496 mg, 5.1 mmol) were added and the reaction was heated to reflux for 3 hours. The product precipitated from the reaction and was filtered off after cooling, washed with ethanol, water and ethanol and dried in vacuo to give the title compound (810 mg, 56%) as a beige solid.
$^1$H NMR (d$^6$-DMSO): δ 1.32 (3H, d), 4.61 (1H, q), 7.39 (1H, s), 7.66 (1H, s), 8.55 (1H, bs), 9.33 (1H, bs).

c) 8-Bromo-6-chloro-4-methyl-2-methylsulfanyl-3,4-dihydro-quinazoline hydroiodide Methyl iodide (0.51 ml, 8.23 mmol) was added to a suspension of 8-bromo-6-chloro-4-methyl-3,4-dihydro-1H-quinazoline-2-thione (800 mg, 2.74 mmol) in acetone (8 ml). The mixture was stirred for 3 hours (r.t.), and the title compound (690 mg, 58%) was isolated from the reaction mixture by filtration.
$^1$H NMR (d$^6$-DMSO): δ 1.40 (3H, d), 2.68 (3H, s), 4.99 (1H, q), 7.44 (1H, s), 7.74 (1H, s), 10.0 (1H, bs), 11.0 (1H, bs).

d) (8-Bromo-6-chloro-4-methyl-3,4-dihydro-quinazolin-2-yl)-(2-phenoxy-ethyl)-amine 8-Bromo-6-chloro-4-methyl-2-methylsulfanyl-3,4-dihydro-quinazoline hydroiodide (141 mg, 0.33 mmol) and 2-phenoxyethyl amine (53.5 mg, 0.39 mmol) were dissolved in acetonitrile (1 ml) and heated to 200° C. in a sealed tube in a microwave oven for 30 minutes. After cooling the reaction was treated with 1N aqueous sodium hydroxide solution, methylene chloride and 5 to 7 drops of 30% aqueous hydrogen peroxide solution. After the reaction has ceased the layers were separated and the aqueous phase was extracted with methylene chloride. The combined organic layers were dried over sodium sulfate, filtered, the solvent was evaporated and the residue was purified by column chromatography (CH$_2$Cl$_2$:MeOH:aq conc NH$_3$=9:1:0.1) to yield the title compound as an off-white solid (60 mg, 47%).
(MS: n/e=394.0, 396.0, 398.1 [M+H$^+$]). $^1$H NMR (CDCl$_3$): δ 1.22 (3H, d); 3.64 (2H, q), 4.12 (2H, t), 4.47 (2H, q), 6.25 (t, 1H), 6.50 (1H, s) 6.89-7.03 (4H, m), 7.25-7.31 (2H, m), 7.35 (1H, s).

EXAMPLE 26

(6-Chloro-4-methyl-3,4-dihydro-quinazolin-2-yl)-(2-phenoxy-ethyl)-amine

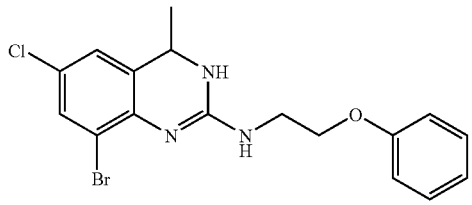

a) [4-Chloro-2-(1-hydroxy-ethyl)-phenyl]-carbamic acid tert-butyl ester

At −78° C. under nitrogen 1.6 M butyllithium solution in hexane (4.89 ml, 7.8 mmol) were added dropwise to [2-bromo-4-chloro-phenyl]-carbamic acid tert-butyl ester (1.09 g, 3.56 mmol) in THF (20 ml). The reaction was stirred for 15 minutes at −78° C. and acetaldehyde (235 mg, 5.33 mmol) was added dropwise. After stirring for 15 minutes at −78° C. saturated aqueous ammonium chloride solution was added and the reaction was allowed to warm to room temperature. The reaction was diluted with water and extracted twice with diethyl ether. The combined organic layers were washed with saturated aqueous sodium chloride solution, dried over sodium sulfate, filtered and the solvent was evaporated to yield the crude product which was purified by column chromatography (heptane:ethyl acetate=4:1). The product was isolated as a colorless viscous oil (525 mg, 54%).

$^1$H NMR (d$^6$-DMSO): δ 1.81 (9H, s), 1.58 (3H, d), 2.15 (1H, d), 4.90 (1H, m), 7.13 (1H, s), 7.22 (1H, d), 7.90 (1H, d), 7.93 (1H, bs).

b) 6-Chloro-4-methyl-3,4-dihydro-1H-quinazoline-2-thione

[4-Chloro-2-(1-hydroxy-ethyl)-phenyl]-carbamic acid tert-butyl ester (525 mg, 1.93 mmol) was suspended in a mixture of ethanol (1.5 ml), water (2.3 ml) and aqueous concentrated hydrogen chloride solution (0.6 ml). Potassium thiocyanate (206 mg, 2.1 mmol) was added and the reaction was heated to reflux for 3 hours. The product precipitated from the reaction and was filtered off after cooling, washed with water and ethanol and dried in vacuo to give the title compound (347 mg, 84%) as a white solid.

$^1$H NMR (d$^6$-DMSO): δ 1.32 (3H, d), 4.56 (1H, q), 6.94 (1H, d), 7.22 (1H, d), 7.25 (1H, s), 8.80 (1H, bs), 10.56 (1H, bs).

c) 6-Chloro-4-methyl-2-methylsulfanyl-3,4-dihydro-quinazoline hydroiodide

Methyl iodide (0.30 ml, 4.86 mmol) was added to a suspension of 6-chloro-4-methyl-3,4-dihydro-1H-quinazoline-2-thione (345 mg, 1.62 mmol) in acetone (4.8 ml). The mixture was stirred for 2 hours (r.t.), diluted with diethyl ether and the title compound (538 mg, 94%) was isolated from the reaction mixture by filtration.

$^1$H NMR (d$^6$-DMSO): δ 1.47 (3H, d), 2.74 (3H, s), 4.99 (1H, q), 7.12 (1H, d), 7.42 (1H, d), 7.47 (1H, s), 10.3 (1H, bs), 12.8 (1H, bs).

d) (6-Chloro-4-methyl-3,4-dihydro-quinazolin-2-yl)-(2-phenoxy-ethyl)-amine

6-Chloro-4-methyl-2-methylsulfanyl-3,4-dihydro-quinazoline hydroiodide (106 mg, 0.30 mmol) and 2-phenoxyethyl amine (168 mg, 1.2 mmol) were dissolved in acetonitrile (0.9 ml) and heated to 170° C. in a sealed tube in a microwave oven for 30 minutes. After cooling the reaction was treated with 1N aqueous sodium hydroxide solution, methylene chloride and 5 to 7 drops of 30% aqueous hydrogen peroxide solution. After the reaction has ceased the layers were separated and the aqueous phase was extracted with methylene chloride. The combined organic layers were dried over sodium sulfate, filtered, the solvent was evaporated and the residue was purified by column chromatography (CH$_2$Cl$_2$:MeOH:aq conc NH$_3$=9:1:0.1) to yield the title compound as a white solid (88 mg, 93%).

(MS: m/e=316.0, 318.0 [M+H$^+$]). $^1$H NMR (CDCl$_3$): δ 1.23 (3H, d), 3.56 (2H, m), 4.05 (2H, t), 4.47 (1H, q), 5.95 (1H, bs), 6.27 (1H, bs), 6.69 (1H, d), 6.90-7.01 (4H, m), 7.29 (2H, t).

EXAMPLE 27

(7-Chloro-4-methyl-3,4-dihydro-quinazolin-2-yl)-(2-phenoxy-ethyl)-amine

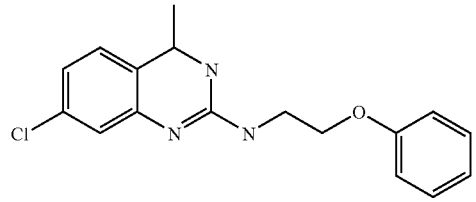

The title compound was prepared in analogy to example 26 from [2-bromo-5-chloro-phenyl]-carbamic acid tert-butyl ester.

$^1$H NMR (CDCl$_3$): δ 1.42 (3H, d), 3.72 (2H, t), 4.11 (2H, t), 4.60 (1H, q), 6.84 (s, 2H), 6.89-7.00 (1H, m) 7.21-7.32 (6H, m).

EXAMPLE 28

(5,8-Dichloro-4-methyl-3,4-dihydro-quinazolin-2-yl)-(2-phenoxy-ethyl)-amine

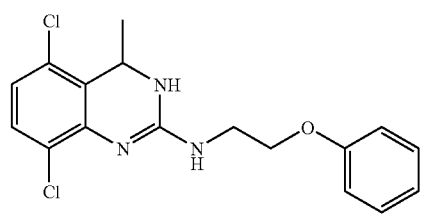

a) 2-Amino-3,6-dichloro-N-methoxy-N-methyl-benzamide

N,O-dimethylhydroxylamine hydrochloride (3.28 g, 33 mmol) and 2-amino-3,6-dichlorobenzoic acid (4.76 g, 22 mmol) were dissolved in DMF (110 ml). N-methylmorpholine (9.99 g, 99 mmol) and HBTU (12.5 g, 33 mmol) were added and the reaction was stirred over night (r.t.). The reaction was poured onto water, extracted twice with diethyl ether. The combined organic layers were dried over sodium sulfate, filtered and the solvent was evaporated. The residue was crystallized with heptane and a little bit of diethyl ether. The filtrate was purified by column chromatography (heptane:ethyl acetate=1:1) to yield the product as an off-white solid (5.52 g, 100%).

$^1$H NMR (d$^6$-DMSO): δ 3.29 (3H, s), 3.50 (3H, s), 5.43 (2H, s), 6.66 (1H, d), 7.26 (1H, d).

b) 1-(2-Amino-3,6-dichloro-phenyl)-ethanone

2-Amino-3,6-dichloro-N-methoxy-N-methyl-benzamide (2491 mg, 10 mmol) were dissolved in THF (100 ml). At −78° C. under nitrogen 1.6 M methyllithium solution in diethyl-ether (25.0 ml, 40 mmol) were added dropwise and the reaction was allowed to reach room temperature and was stirred over night. The reaction was cooled in an icebath and 2N aqueous hydrogen chloride solution (30 ml) were added and the reaction was stirred for 30 min (r.t.). The reaction was diluted with water and extracted twice with diethyl ether. The combined organic layers were washed with saturated aqueous sodium chloride solution, dried over sodium sulfate, filtered and the solvent was evaporated. The residue was purified by column chromatography (CH$_2$Cl$_2$) to yield the product as an orange oil (565 mg, 28%).

$^1$H NMR (CDCl$_3$): δ 2.65 (3H, s), 5.32 (2H, bs), 6.69 (1H, d), 7.21 (1H, d).

c) 5,8-Dichloro-4-methyl-3,4-dihydro-1H-quinazoline-2-thione 1-(2-Amino-3,6-dichloro-phenyl)-ethanone (1160 mg, 57 mmol) was dissolved in ethanol (12 ml). At 65° C. under nitrogen sodium borohydride (129 mg, 34 mmol) was added and the reaction was heated over night to 65° C. Water (6 ml) potassium thiocyanate (608 mg, 63 mmol) in water (3.6 ml) and concentrated aqueous hydrogen chloride solution (3.6 ml diluted with 4.8 ml water) were added. An oil precipitated and the reaction was heated to 95° C. for 3 hours. After cooling the product was filtered off, washed with water and ethanol to yield a light yellow solid (963 mg, 69%).

$^1$H NMR (d$^6$-DMSO): δ 1.28 (3H, d), 4.61 (1H, m), 7.19 (1H, d), 7.44 (1H, d), 9.32 (1H, s), 9.41 (1H, s).

d) 5,8-Dichloro-4-methyl-2-methylsulfanyl-3,4-dihydro-quinazoline hydroiodide 5,8-Dichloro-4-methyl-3,4-dihydro-1H-quinazoline-2-thione (963 mg, 3.9 mmol) was suspended in acetone (12 ml). Methyl iodide (0.73 ml, 11.7 mmol) was added and the reaction stirred over night (r.t.). The reaction was diluted with diethyl ether, the product was filtered and dried in vacuo to yield a white solid (1307 mg, 86%)

$^1$H NMR (d$^6$-DMSO): δ 1.29 (3H, d), 2.63 (3H, s), 4.80 (1H, q), 7.26 (1H, d), 7.46 (1H, d).

e) (5,8-Dichloro-4-methyl-3,4-dihydro-quinazolin-2-yl)-(2-phenoxy-ethyl)-amine 5,8-Dichloro-4-methyl-2-methylsulfanyl-3,4-dihydro-quinazoline hydroiodide (116 mg, 0.30 mmol) and 2-phenoxyethyl amine (126 mg, 0.9 mmol) were dissolved in acetonitrile (0.9 ml) and heated to 170° C. in a sealed tube in a microwave oven for 30 minutes. After cooling the reaction was treated with 1N aqueous sodium hydroxide solution (0.9 ml) and 5 to 7 drops of 30% aqueous hydrogen peroxide solution. The reaction was diluted with water and the product precipitated as a white solid, which was filtered off, washed with water and dried in vacuo to yield the title compound (98 mg, 93%).

(MS: m/e=350.2, 352.2 [M+H$^+$]). $^1$H NMR (d$^6$-DMSO): δ 1.07 (3H, d), 3.57 (2H, q), 4.05 (2H, t), 4.55 (1H, q), 6.39 (1H, t), 6.59 (1H, s), 6.72 (1H, d), 6.86 (1H, t), 6.92 (2H, d), 7.11 (1H, d), 7.22 (2H, t).

EXAMPLE 29

(6-Fluoro-3,4-dihydro-quinazolin-2-yl)-[2-(2-methoxy-phenoxy)-ethyl]-amine

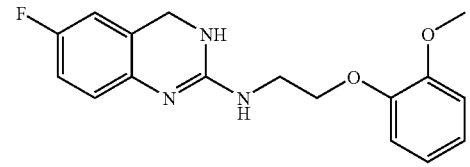

The title compound (MS: m/e=316.1 [M+H$^+$]) was prepared in analogy to example 1 from 2-aminomethyl-4-fluoro-phenylamine.

$^1$H NMR (CDCL$_3$): δ 3.64 (2H, t), 3.87 (3H, s), 4.48 (2H, s), 6.61 (1H, d), 6.79-6.97 (6H, m).

EXAMPLE 30

(3,4-Dihydro-quinazolin-2-yl)-((S)-1-methyl-2-phenoxy-ethyl)-amine

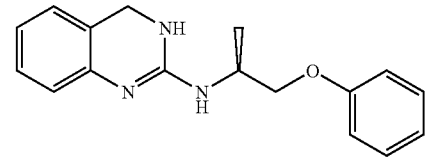

The title compound (MS: m/e=282.4 [M+H$^+$]) was prepared in analogy to example 1 from (S)-2-(boc-amino)-1-propanol and phenol.

EXAMPLE 31

(3,4-Dihydro-quinazolin-2-yl)-((R)-1-methyl-2-phenoxy-ethyl)-amine

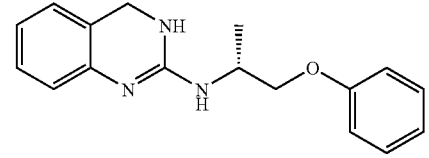

The title compound (MS: m/e=282.4 [M+H$^+$]) was prepared in analogy to example 1 from (R)-2-(boc-amino)-1-propanol and phenol.

EXAMPLE 32

(3,4-Dihydro-quinazolin-2-yl)-[2-(2-phenoxy-phenoxy)-ethyl]-amine

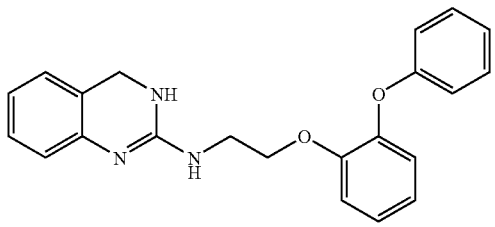

The title compound (MS: m/e=360.4 [M+H$^+$]) was prepared in analogy to example 1 from 2-phenoxy-phenol.

EXAMPLE 33

(3,4-Dihydro-quinazolin-2-yl)-[2-(2-isopropoxy-phenoxy)-ethyl]-amine

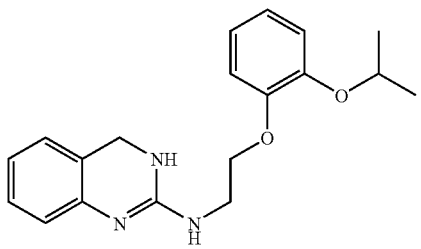

The title compound (MS: m/e=326.4 [M+H$^+$]) was prepared in analogy to example 1 from 2-isopropoxyphenol.

EXAMPLE 34

(3,4-Dihydro-quinazolin-2-yl)-[2-(2-propenyl-phenoxy)-ethyl]-amine

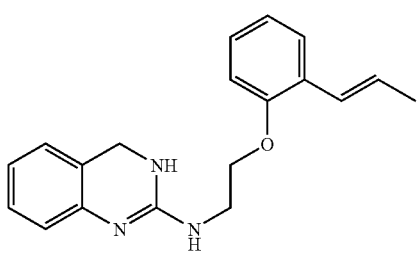

The title compound (MS: m/e=308.4 [M+H$^+$]) was prepared in analogy to example 1 from 2-propenylphenol.

EXAMPLE 35

(3,4-Dihydro-quinazolin-2-yl)-[2-(2-methylsulfanyl-phenoxy)-ethyl]-amine

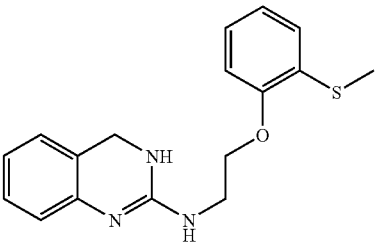

The title compound (MS: m/e=314.0 [M+H$^+$]) was prepared in analogy to example 1 from (2-hydroxy)thioanisol.

EXAMPLE 36

(4-Methyl-3,4-dihydro-benzo[h] quinazolin-2-yl)-(2-phenoxy-ethyl)-amine

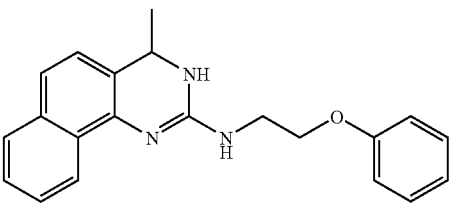

The title compound (MS: m/e=332.3 [M+H$^+$]) was prepared in analogy to example 11 from 1-(1-amino-naphthalen-2-yl)-ethanone. 1-(1-Amino-naphthalen-2-yl)-ethanone can be obtained by the method of Katsuhara, Yutaka; Maruyama, Hirokazu; Shigemitsu, Yasuo; Odaira, Yoshinobu: *Tetrahedron Lett.* 1973, 16, 1323-6.

EXAMPLE 37

[2-(2-Bromo-phenoxy)-ethyl]-(3,4-dihydro-quinazolin-2-yl)-amine

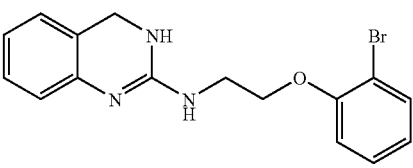

The title compound (MS: m/e=348.4 [M+H$^+$]) was prepared in analogy to example 1 from 2-bromophenol.

EXAMPLE 38

2-[2-(3,4-Dihydro-quinazolin-2-ylamino)-ethoxy]-benzonitrile

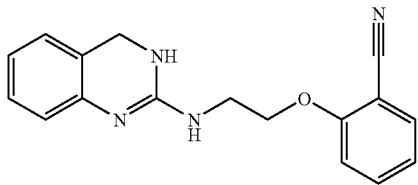

The title compound (MS: m/e=293.1 [M+H$^+$]) was prepared in analogy to example 1 from 2-hydroxybenzonitrile.

EXAMPLE 39

[2-(2-Benzyloxy-phenoxy)-ethyl]-(3,4-dihydro-quinazolin-2-yl)-amine

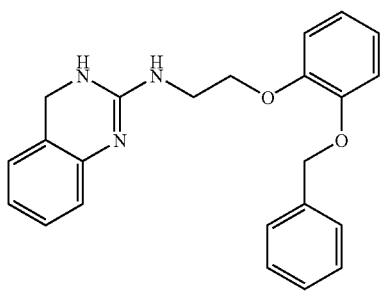

The title compound (MS: m/e=374.4 [M+H$^+$]) was prepared in analogy to example 1 from 2-hydroxybenzonitrile 2-(2-benzyloxyphenoxy)ethylamine.

EXAMPLE 40

(3,4-Dihydro-quinazolin-2-yl)-[2-(2-ethyl-phenoxy)-ethyl]-amine

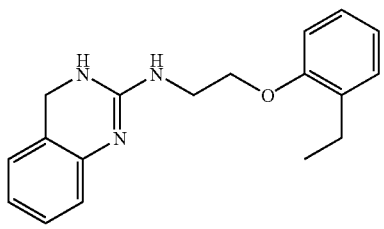

The title compound (MS: m/e=296.5 [M+H$^+$]) was prepared in analogy to example 1 from 2-ethylphenol.

EXAMPLE 41

(3,4-Dihydro-quinazolin-2-yl)-[2-(2,6-dimethoxy-phenoxy)-ethyl]-amine

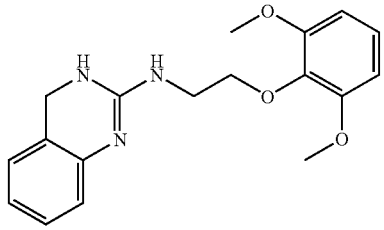

The title compound (MS: m/e=328.3 [M+H$^+$]) was prepared in analogy to example 1 from 2,6-dimethoxyphenol.

EXAMPLE 42

(3,4-Dihydro-quinazolin-2-yl)-[2-(2,3-dimethoxy-phenoxy)-ethyl]-amine

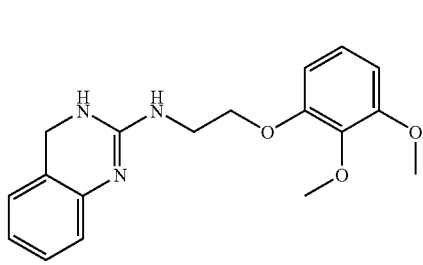

The title compound (MS: m/e=328.3 [M+H$^+$]) was prepared in analogy to example 1 from 2,3-dimethoxyphenol.

EXAMPLE 43

2-[2-(3,4-Dihydro-quinazolin-2-ylamino)-ethoxy]-3-methoxy-benzonitrile

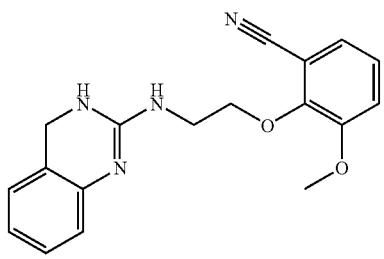

The title compound (MS: m/e=323.5 [M+H$^+$]) was prepared in analogy to example 1 from 2-hydroxy-3-methoxy-benzonitrile.

EXAMPLE 44

(3,4-Dihydro-quinazolin-2-yl)-[2-(2-methoxy-5-methyl-phenoxy)-ethyl]-amine

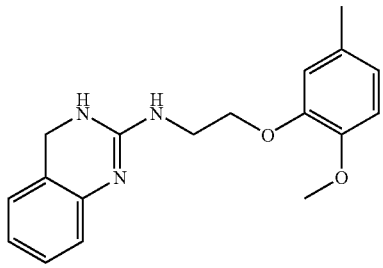

The title compound (MS: m/e=312.3 [M+H$^+$]) was prepared in analogy to example 1 from 2-methoxy-5-methylphenol.

EXAMPLE 45

(3,4-Dihydro-quinazolin-2-yl)-[2-(2-fluoro-6-methoxy-phenoxy)-ethyl]-amine

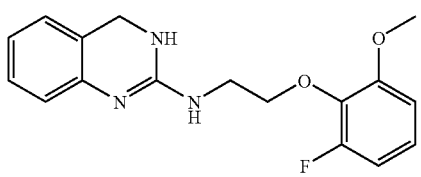

The title compound (MS: m/e=316.1 [M+H$^+$]) was prepared in analogy to example 1 from 2-fluoro-6-methoxyphenol.

EXAMPLE 46

[2-(2-Bromo-5-fluoro-phenoxy)-ethyl]-(3,4-dihydro-quinazolin-2-yl)-amine

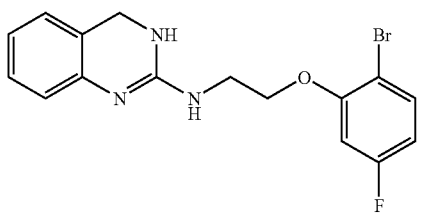

The title compound (MS: m/e=364.0 [M+H$^+$]) was prepared in analogy to example 1 from 2-bromo-5-fluorophenol.

EXAMPLE 47

[2-(2,6-Dichloro-phenoxy)-ethyl]-(3,4-dihydro-quinazolin-2-yl)-amine

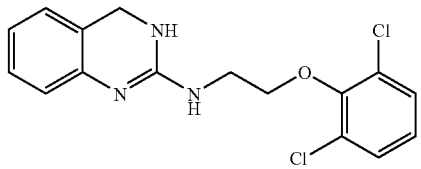

The title compound (MS: m/e=336.3 [M+H$^+$]) was prepared in analogy to example 1 from 2,6-dichlorophenol.

EXAMPLE 48

(3,4-Dihydro-quinazolin-2-yl)-[2-(2-isopropyl-phenoxy)-ethyl]-amine

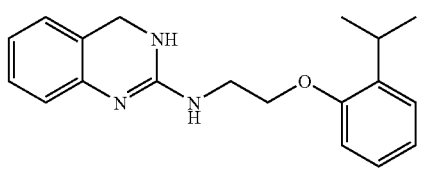

The title compound (MS: m/e=310.4 [M+H$^+$]) was prepared in analogy to example 1 from 2-isopropylphenol.

EXAMPLE 49

[2-(2-Benzyl-phenoxy)-ethyl]-(3,4-dihydro-quinazolin-2-yl)-amine

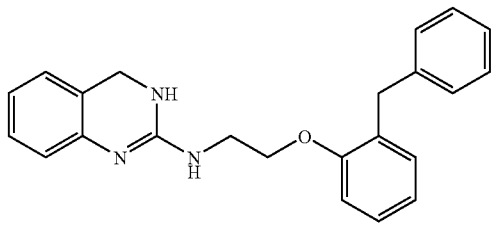

The title compound (MS: m/e=358.4 [M+H$^+$]) was prepared in analogy to example 1 from 2-benzylphenol.

EXAMPLE 50

[4-(2,5-Dichloro-phenyl)-3,4-dihydro-quinazolin-2-yl]-(2-phenoxy-ethyl)-amine

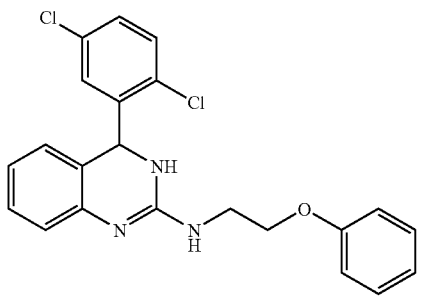

The title compound (MS: m/e=412.1 [M+H⁺]) was prepared in analogy to example 11 from (2-amino-phenyl)-(2,5-dichloro-phenyl)-methanone. (2-Amino-phenyl)-(2,5-dichloro-phenyl)-methanone can be obtained by the method of Kamal, Ahmed; Arifuddin, M.; Rao, N. Venugopal: *Synthetic Communications* 1998, 28(21), 3927-3931.

EXAMPLE 51

[6-Chloro-4-(2-chloro-phenyl)-3,4-dihydro-quinazolin-2-yl]-(2-phenoxy-ethyl)-amine

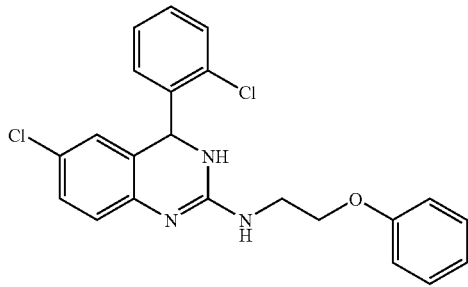

The title compound (MS: m/e=412.4 [M+H⁺]) was prepared in analogy to example 11 from (2-Amino-5-chloro-phenyl)-(2-chloro-phenyl)-methanone.

EXAMPLE 52

[2-(2-Chloro-3,5-difluoro-phenoxy)-ethyl]-(3,4-dihydro-quinazolin-2-yl)-amine

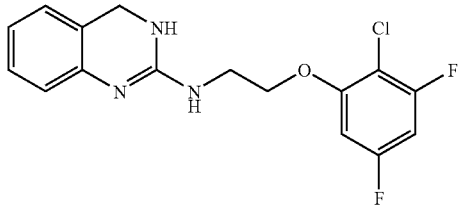

The title compound (MS: m/e=338.1 [M+H⁺]) was prepared in analogy to example 1 from 2-chloro-3,5-difluorophenol.

EXAMPLE 53

[2-(2-Chloro-3,6-difluoro-phenoxy)-ethyl]-(3,4-dihydro-quinazolin-2-yl)-amine

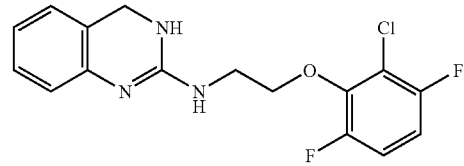

The title compound (MS: m/e=338.1 [M+H⁺]) was prepared in analogy to example 1 from 2-chloro-3,6-difluorophenol.

EXAMPLE 54

(2-Phenoxy-ethyl)-(4-thiophen-3-yl-3,4-dihydro-quinazolin-2-yl)-amine

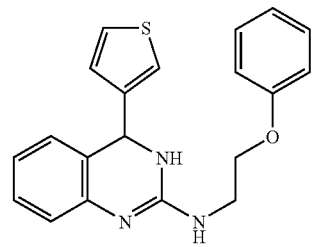

The title compound (MS: m/e=350.5 [M+H⁺]) was prepared in analogy to example 11 from (2-amino-phenyl)-thiophen-3-yl-methanone. (2-Amino-phenyl)-thiophen-3-yl-methanone can be obtained by the method of Hunziker, Fritz; Fischer, Rudolf; Kipfer, Peter; Schmutz, Jean; Buerki, Hans R.; Eichenberger, Erwin; White, Trevor G.: *Europ. J. Med. Chem.* 1981, 16(5), 391-8.

EXAMPLE 55

[4-(3,5-Dimethyl-isoxazol-4-yl)-3,4-dihydro-quinazolin-2-yl]-(2-phenoxy-ethyl)-amine

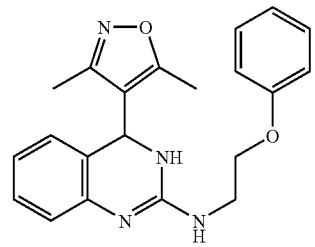

The title compound (MS: m/e=363.4 [M+H⁺]) was prepared in analogy to example 11 from (2-amino-phenyl)-(3,5-

EXAMPLE 56

[2-(2-Chloro-phenoxy)-ethyl]-(6-methoxy-3,4-dihydro-quinazolin-2-yl)-amine

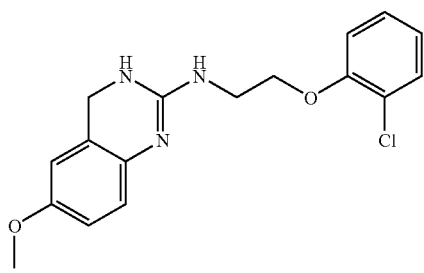

The title compound (MS: m/e=332.3 [M+H$^+$]) was prepared in analogy to example 1 from 2-aminomethyl-4-methoxy-phenylamine and 2-chlorophenol.

EXAMPLE 57

(7-Chloro-3,4-dihydro-quinazolin-2-yl)-[2-(2-chloro-phenoxy)-ethyl]-amine

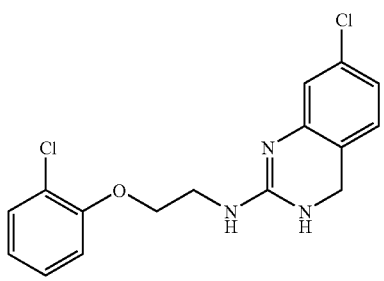

The title compound (MS: m/e=336.3 [M+H$^+$]) was prepared in analogy to example 1 from 2-aminomethyl-5-chloro-phenylamine and 2-chlorophenol.

EXAMPLE 58

[2-(2-Chloro-phenoxy)-ethyl]-(6-methyl-3,4-dihydro-quinazolin-2-yl)-amine

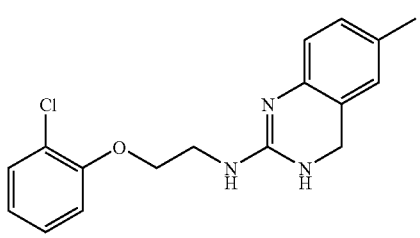

The title compound (MS: m/e=316.0 [M+H$^+$]) was prepared in analogy to example 1 from 2-aminomethyl-4-methyl-phenylamine and 2-chlorophenol.

EXAMPLE 59

[2-(2-Chloro-phenoxy)-ethyl]-(5-fluoro-3,4-dihydro-quinazolin-2-yl)-amine

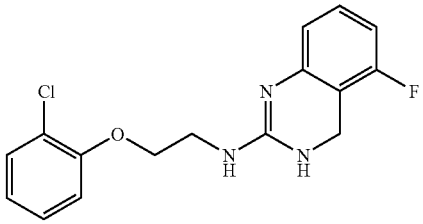

The title compound (MS: m/e=320.1 [M+H$^+$]) was prepared in analogy to example 1 from 2-aminomethyl-3-fluoro-phenylamine and 2-chlorophenol.

EXAMPLE 60

[2-(2-Chloro-phenoxy)-ethyl]-(6-chloro-4-phenyl-3,4-dihydro-quinazolin-2-yl)-amine

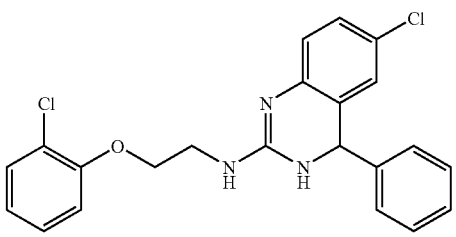

The title compound (MS: m/e=412.4 [M+H$^+$]) was prepared in analogy to example 11 from (2-amino-5-chloro-phenyl)-phenyl-methanone and 2-chlorophenol.

EXAMPLE 61

[2-(2-Chloro-phenoxy)-ethyl]-(4-phenyl-3,4-dihydro-quinazolin-2-yl)-amine

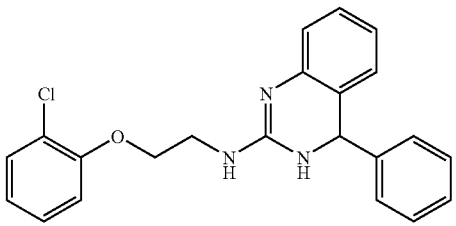

The title compound (MS: m/e=378.3 [M+H$^+$]) was prepared in analogy to example 11 from (2-amino-phenyl)-phenyl-methanone and 2-chlorophenol.

EXAMPLE 62

(6-Methoxy-3,4-dihydro-quinazolin-2-yl)-[2-(2-methoxy-phenoxy)-ethyl]-amine

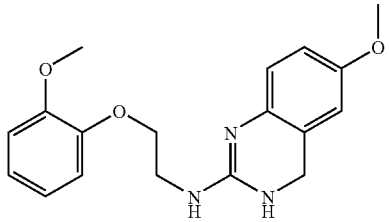

The title compound (MS: m/e=328.3 [M+H$^+$]) was prepared in analogy to example 1 from 2-aminomethyl-4-methoxy-phenylamine.

EXAMPLE 63

(7-Chloro-3,4-dihydro-quinazolin-2-yl)-[2-(2-methoxy-phenoxy)-ethyl]-amine

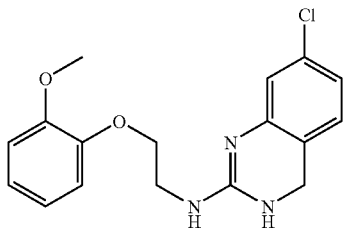

The title compound (MS: m/e=332.3 [M+H$^+$]) was prepared in analogy to example 1 from 2-aminomethyl-5-chloro-phenylamine.

EXAMPLE 64

[2-(2-Methoxy-phenoxy)-ethyl]-(6-methyl-3,4-dihydro-quinazolin-2-yl)-amine

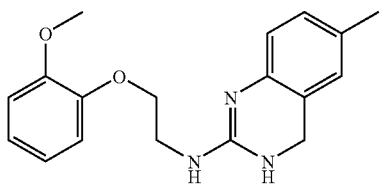

The title compound (MS: m/e=312.4 [M+H$^+$]) was prepared in analogy to example 1 from 2-aminomethyl-4-methyl-phenylamine.

EXAMPLE 65

(6-Chloro-4-phenyl-3,4-dihydro-quinazolin-2-yl)-[2-(2-methoxy-phenoxy)-ethyl]-amine

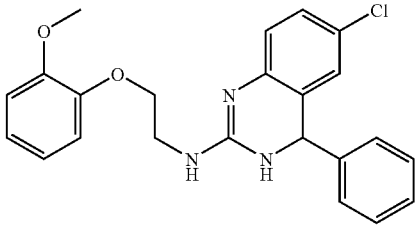

The title compound (MS: m/e=408.4 [M+H$^+$]) was prepared in analogy to example 11 from (2-amino-5-chloro-phenyl)-phenyl-methanone.

EXAMPLE 66

[2-(2-Methoxy-phenoxy)-ethyl]-(4-phenyl-3,4-dihydro-quinazolin-2-yl)-amine

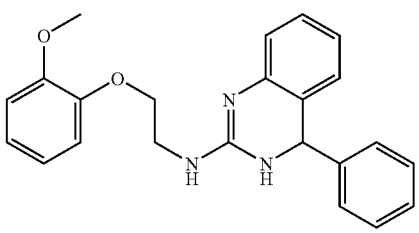

The title compound (MS: m/e=374.4 [M+H$^+$]) was prepared in analogy to example 1 from (2-amino-phenyl)-phenyl-methanone.

EXAMPLE 67

(5-Fluoro-3,4-dihydro-quinazolin-2-yl)-[2-(2-methoxy-phenoxy)-ethyl]-amine

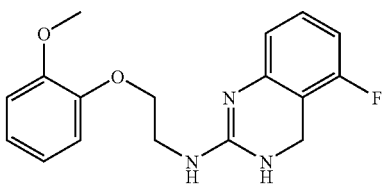

The title compound (MS: m/e=316.1 [M+H$^+$]) was prepared in analogy to example 1 from 2-aminomethyl-3-fluoro-phenylamine.

EXAMPLE 68

(4-Methyl-7-trifluoromethyl-3,4-dihydro-quinazolin-2-yl)-(2-phenoxy-ethyl)-amine

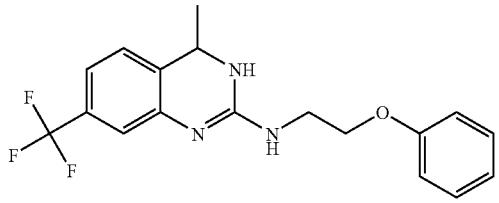

a) N,N'-bis(tert-butyloxycarbonyl)-2-bromo-5-trifluoromethylaniline

3-Amino-4-bromobenzotrifluorid (4.90 g, 20 mmol) and DMAP (244 mg, 2 mmol) were dissolved in THF (140 ml). At room temperature under nitrogen a solution of di-tert-butyl-dicarbonate (9.60 g, 44 mmol) dissolved in THF (60 ml) was added and the solution was stirred at room temperature over night. The solvent was removed in vacuo. The residue was dissolved in diethyl ether and extracted once with ice cold 1N aqueous HCl solution and once with saturated aqueous sodium chloride solution. The organic layer was dried over sodium sulfate, filtered and the solvent was removed to yield the product (8.49 g, 96%) as a yellow viscous oil sufficiently pure enough to be used without further purification in the next step.

$^1$H NMR (CDCl$_3$): δ 1.41 (18H, s), 7.14 (1H, d), 7.49 (1H, s), 7.77 (1H, d).

a) (2-Bromo-5-trifluoromethyl-phenyl)-carbamic acid tert-butyl ester

N,N'-bis(tert-butyloxycarbonyl)-2-bromo-5-trifluoromethylaniline (8.49 g, 19.5 mmol) were dissolved in methanol (195 ml). Potassium carbonate (8.09 g, 58.5 mmol) were added and the reaction was heated for 2 hours to reflux. After cooling to room temperature the reaction was filtered, the solid was washed with methanol and the solvent was evaporated in vacuo. The residue was dissolved in diethyl ether and extracted once with ice cold 1N aqueous HCl solution and once with saturated aqueous sodium chloride solution. The organic layer was dried over sodium sulfate, filtered and the solvent was removed to yield the product (6.78 g, 97%) as a yellow viscous oil sufficiently pure enough to be used without further purification in the next step.

$^1$H NMR (CDCl$_3$): δ 1.55 (9H, s), 7.13 (1H, d), 7.15 (1H, s), 7.62 (1H, d), 8.51 (1H, br s).

a) [2-(1-Hydroxy-ethyl)-5-trifluoromethyl-phenyl]-carbamic acid tert-butyl ester At –78° C. under nitrogen 1.6 M butyllithium solution in hexane (13.8 ml, 20 mmol) were added dropwise to (2-Bromo-5-trifluoromethyl-phenyl)-carbamic acid tert-butyl ester (3.4 g, 10 mmol) in THF (60 ml). The reaction was stirred for 15 minutes at –78° C. and acetaldehyde (881 mg, 20 mmol) was added dropwise. After stirring for 15 minutes at –78° C. saturated aqueous ammonium chloride solution was added and the reaction was allowed to warm to room temperature. The reaction was diluted with water and extracted twice with diethyl ether. The combined organic layers were washed with saturated aqueous sodium chloride solution, dried over sodium sulfate, filtered and the solvent was evaporated to yield the crude product which was purified by column chromatography (heptane:ethyl acetate=7:3). The product was isolated as a yellow viscous oil (1.78 g, 58%).

$^1$H NMR (CDCl$_3$): δ 1.53 (9H, s), 1.60 (3H, d), 2.19 (1H, d), 5.03 (1H, m), 7.23 (2H, s), 8.24 (1H, br s), 8.37 (1H, s).

b) 4-Methyl-7-trifluoromethyl-3,4-dihydro-1H-quinazoline-2-thione 2-(1-Hydroxy-ethyl)-5-trifluoromethyl-phenyl]-carbamic acid tert-butyl ester (153 mg, 0.5 mmol) was suspended in a mixture of ethanol (0.4 ml), water (0.6 ml) and aqueous concentrated hydrogen chloride solution (0.15 ml). Potassium thiocyanate (53 mg, 0.55 mmol) was added and the reaction was heated to reflux for 3 hours. The product precipitated from the reaction and was filtered off after cooling, washed with water and ethanol and dried in vacuo to give the title compound (90 mg, 73%) as a white solid.

$^1$H NMR (d$^6$-DMSO): δ 1.35 (3H, d), 4.65 (1H, q), 7.32 (1H, d), 7.38 (1H, d), 8.95 (1H, bs), 10.68 (1H, bs).

c) 4-Methyl-2-methylsulfanyl-7-trifluoromethyl-3,4-dihydro-quinazoline hydroiodide Methyl iodide (0.94 ml, 15.1 mmol) was added to a suspension of 4-methyl-7-trifluoromethyl-3,4-dihydro-1H-quinazoline-2-thione (1.24 g, 5.04 mmol) in acetone (15 ml). The mixture was stirred for 3 hours (r.t.), diluted with diethyl ether and the title compound (1.66 g, 85%) was isolated from the reaction mixture by filtration as a white solid.

$^1$H NMR (d$^6$-DMSO): δ 1.49 (3H, d), 2.76 (3H, s), 5.10 (1H, q), 7.56 (1H, d), 7.64 (1H, d), 10.5 (1H, bs), 12.5 (1H, bs).

d) (4-Methyl-7-trifluoromethyl-3,4-dihydro-quinazolin-2-yl)-(2-phenoxy-ethyl)-amine 4-Methyl-2-methylsulfanyl-7-trifluoromethyl-3,4-dihydro-quinazoline hydroiodide (116 mg, 0.30 mmol) and 2-phenoxyethyl amine (126 mg, 0.9 mmol) were dissolved in acetonitrile (0.9 ml) and heated to 170° C. in a sealed tube in a microwave oven for 30 minutes. After cooling the reaction was treated with 1N aqueous sodium hydroxide solution, methylene chloride and 5 to 7 drops of 30% aqueous hydrogen peroxide solution. After the reaction has ceased the reaction was diluted with little water and the precipitated product was filtered off, washed with water, dried in vacuo to yield the title compound as a white solid (104 mg, 94%).

(MS: m/e=350.2, 351.1 [M+H$^+$]). $^1$H NMR (CDCl$_3$): δ 1.25 (3H, d), 3.58 (2H, m), 4.05 (2H, t), 4.55 (1H, q), 6.08 (1H, bt), 6.37 (1H, s), 6.91-7.01 (5H, m), 7.11 (1H, d), 7.29 (2H, t).

The invention claimed is:

1. A compound of formula I

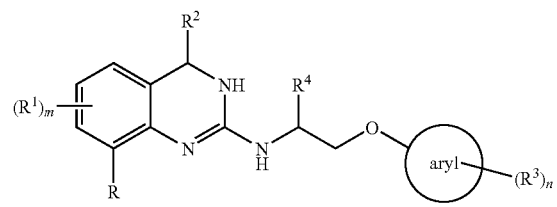

wherein
- R¹ is hydrogen, lower alkyl, lower alkoxy, halogen or lower alkyl substituted by halogen;
- R is hydrogen or halogen; or
- R¹ and R are together with the carbon atoms to which they are attached —CH=CH—CH=CH—;
- R² is hydrogen, lower alkyl, phenyl optionally substituted by halogen, or hetaryl optionally substituted by lower alkyl;
- R³ is hydrogen, lower alkyl, phenyl, benzyl, lower alkenyl, lower alkoxy, phenyloxy, benzyloxy, S-lower alkyl, halogen, CN, lower alkyl substituted by halogen or O-lower alkyl substituted by halogen;
- R⁴ is hydrogen or lower alkyl;
- aryl is phenyl or naphthyl;
- n is 1, 2 or 3; and
- m is 1 or 2;

or a pharmaceutically acceptable acid addition salt or tautomeric form thereof.

2. A compound of claim 1, wherein aryl is phenyl.

3. A compound of claim 2, wherein aryl is unsubstituted phenyl.

4. A compound of claim 3, wherein R² is hydrogen and aryl is unsubstituted phenyl.

5. A compound of claim 4, wherein R¹ is hydrogen, halogen, methyl, or methoxy.

6. A compound of claim 5, wherein R, R¹, R², R³, and R⁴ are hydrogen.

7. A compound of claim 4, selected from the group consisting of
- (6-fluoro-3,4-dihydro-quinazolin-2-yl)-(2-phenoxy-ethyl)-amine,
- (6-methyl-3,4-dihydro-quinazolin-2-yl)-(2-phenoxy-ethyl)-amine,
- (3,4-dihydro-quinazolin-2-yl)-(2-phenoxy-ethyl)-amine,
- (5-fluoro-3,4-dihydro-quinazolin-2-yl)-(2-phenoxy-ethyl)-amine,
- (5-chloro-3,4-dihydro-quinazolin-2-yl)-(2-phenoxy-ethyl)-amine,
- (5-methyl-3,4-dihydro-quinazolin-2-yl)-(2-phenoxy-ethyl)-amine,
- (5,6-dichloro-3,4-dihydro-quinazolin-2-yl)-(2-phenoxy-ethyl)-amine and
- (6-methoxy-3,4-dihydro-quinazolin-2-yl)-(2-phenoxy-ethyl)-amine.

8. A compound of claim 3, wherein R² is alkyl and aryl is unsubstituted phenyl.

9. A compound of claim 8, which compound is (4-methyl-3,4-dihydro-quinazolin-2-yl)-(2-phenoxy-ethyl)-amine.

10. A compound of claim 3, wherein R² is hetaryl optionally substituted by lower alkyl and aryl is unsubstituted phenyl.

11. A compound of claim 10, wherein R² is a thiophenyl or an isoxazolyl.

12. A compound of claim 3, wherein R² is phenyl optionally substituted by halogen.

13. A compound of claim 2, wherein aryl is substituted phenyl.

14. A compound of claim 13, wherein R¹ is methoxy, halogen, or methyl.

15. A compound of claim 13, wherein R, R¹, R², R³, and R⁴ are hydrogen.

16. A compound of claim 13, wherein n is 2.

17. A compound of claim 13, wherein R² is hydrogen and aryl is phenyl, substituted by lower alkyl, lower alkenyl, lower alkoxy, benzyloxy, S-lower alkyl, halogen, CN, or O-lower alkyl substituted by halogen.

18. A compound of claim 6, selected from the group consisting of
- (3,4-dihydro-quinazolin-2-yl)-[2-(2-methoxy-phenoxy)-ethyl]-amine,
- [2-(2-chloro-phenoxy)-ethyl]-(3,4-dihydro-quinazolin-2-yl)-amine,
- (3,4-dihydro-quinazolin-2-yl)-[2-(2-fluoro-phenoxy)-ethyl]-amine,
- (3,4-dihydro-quinazolin-2-yl)-[2-(2-ethoxy-phenoxy)-ethyl]-amine,
- (3,4-dihydro-quinazolin-2-yl)-(2-m-tolyloxy-ethyl)-amine,
- (3,4-dihydro-quinazolin-2-yl)-[2-(2-trifluoromethoxy-phenoxy)-ethyl]-amine,
- (3,4-dihydro-quinazolin-2-yl)-[2-(3-methoxy-phenoxy)-ethyl]-amine,
- (3,4-dihydro-quinazolin-2-yl)-[2-(3-fluoro-phenoxy)-ethyl]-amine,
- [2-(3-chloro-phenoxy)-ethyl]-(3,4-dihydro-quinazolin-2-yl)-amine,
- (6-fluoro-3,4-dihydro-quinazolin-2-yl)-[2-(2-methoxy-phenoxy)-ethyl]-amine,
- (3,4-dihydro-quinazolin-2-yl)-[2-(2-propenyl-phenoxy)-ethyl]-amine,
- (3,4-dihydro-quinazolin-2-yl)-[2-(2-methylsulfanyl-phenoxy)-ethyl]-amine, and
- [2-(2-bromo-phenoxy)-ethyl]-(3,4-dihydro-quinazolin-2-yl)-amine.

19. A compound of claim 1, wherein aryl is naphthyl.

20. A compound of claim 19, wherein R, R¹, R², R³, and R⁴ are hydrogen.

21. A compound of claim 1, wherein R¹ and R are together with the carbon atoms to which they are attached —CH=CH—CH=CH—.

22. A compound of claim 1, wherein R¹ is lower alkyl, lower alkoxy, halogen or lower alkyl substituted by halogen.

23. A pharmaceutical composition comprising a therapeutically effective amount of a compound of formula I

I wherein
- R¹ is hydrogen, lower alkyl, lower alkoxy, halogen or lower alkyl substituted by halogen;
- R is hydrogen or halogen; or
- R¹ and R are together with the carbon atoms to which they are attached —CH=CH—CH=CH—;
- R² is hydrogen, lower alkyl, phenyl optionally substituted by halogen, or hetaryl optionally substituted by lower alkyl;
- R³ is hydrogen, lower alkyl, phenyl, benzyl, lower alkenyl, lower alkoxy, phenyloxy, benzyloxy, S-lower alkyl, halogen, CN, lower alkyl substituted by halogen or O-lower alkyl substituted by halogen;
- R⁴ is hydrogen or lower alkyl;
- aryl is phenyl or naphthyl;

n is 1, 2 or 3; and m is 1 or 2;

or a pharmaceutically acceptable acid addition salt or tautomeric form thereof and a pharmaceutically acceptable carrier.

24. A compound of claim 6, selected from the group consisting of

- 2-[2-(3,4-dihydro-quinazolin-2-ylamino)-ethoxy]-benzonitrile,
- [2-(2-benzyloxy-phenoxy)-ethyl]-(3,4-dihydro-quinazolin-2-yl)-amine,
- (3,4-dihydro-quinazolin-2-yl)-[2-(2,6-dimethoxy-phenoxy)-ethyl]-amine,
- (3,4-dihydro-quinazolin-2-yl)-[2-(2-methoxy-5-methyl-phenoxy)-ethyl]-amine,
- (3,4-dihydro-quinazolin-2-yl)-[2-(2-fluoro-6-methoxy-phenoxy)-ethyl]-amine,
- [2-(2-bromo-5-fluoro-phenoxy)-ethyl]-(3,4-dihydro-quinazolin-2-yl)-amine,
- [2-(2-chloro-phenoxy)-ethyl]-(6-methoxy-3,4-dihydro-quinazolin-2-yl)-amine,
- [2-(2-chloro-phenoxy)-ethyl]-(6-methyl-3,4-dihydro-quinazolin-2-yl)-amine,
- [2-(2-chloro-phenoxy)-ethyl]-(5-fluoro-3,4-dihydro-quinazolin-2-yl)-amine,
- (6-methoxy-3,4-dihydro-quinazolin-2-yl)-[2-(2-methoxy-phenoxy)-ethyl]-amine,
- [2-(2-methoxy-phenoxy)-ethyl]-(6-methyl-3,4-dihydro-quinazolin-2-yl)-amine and
- (5-fluoro-3,4-dihydro-quinazolin-2-yl)-[2-(2-methoxy-phenoxy)-ethyl]-amine.

* * * * *